United States Patent
Berthon-Jones

(10) Patent No.: US 6,484,719 B1
(45) Date of Patent: Nov. 26, 2002

(54) METHOD FOR PROVIDING VENTILATORY ASSISTANCE IN A SPONTANEOUSLY BREATHING SUBJECT

(75) Inventor: Michael Berthon-Jones, Leonay (AU)

(73) Assignee: ResMed, Inc., NSW (AU)

( * ) Notice: Subject to any disclaimer, the term of this patent is extended or adjusted under 35 U.S.C. 154(b) by 0 days.

(21) Appl. No.: 09/549,197

(22) Filed: Apr. 13, 2000

Related U.S. Application Data

(62) Division of application No. 08/935,785, filed as application No. PCT/AU97/00517 on Aug. 14, 1997.

(30) Foreign Application Priority Data

Sep. 23, 1996 (AU) .............................................. PO2474

(51) Int. Cl.[7] .............................................. A61M 16/00
(52) U.S. Cl. ............................. 128/204.23; 128/204.21; 128/204.18
(58) Field of Search .................. 128/204.18, 204.21, 128/204.23, 202.22, 200.24

(56) References Cited

U.S. PATENT DOCUMENTS

| | | | | |
|---|---|---|---|---|
| 4,957,107 A | * | 9/1990 | Sipin ..................... | 128/204.21 |
| 5,313,937 A | * | 5/1994 | Zdrojkowski .......... | 128/202.22 |
| 5,799,652 A | * | 9/1998 | Kotliar .................. | 128/205.11 |
| 6,152,129 A | * | 11/2000 | Berthon-Jones ........ | 128/204.23 |
| 6,257,234 B1 | * | 7/2001 | Sun ....................... | 128/204.18 |
| 6,286,508 B1 | * | 9/2001 | Remmers et al. ...... | 128/204.18 |
| 6,318,365 B1 | * | 11/2001 | Vogele et al. .......... | 128/204.18 |

FOREIGN PATENT DOCUMENTS

EP                  0 651 971 A    *    5/1995

* cited by examiner

Primary Examiner—Aaron J. Lewis
(74) Attorney, Agent, or Firm—Gottlieb, Rackman & Reisman, P.C.

(57) ABSTRACT

The apparatus provides for the determination of the instantaneous phase in the respiratory cycle, subject's average respiration rate and the provision of ventilatory assistance. A microprocessor (16) receives an airflow signal from a pressure transducer (18) coupled to a port (27) at a mask (11). The microprocessor (16) controls a servo (19), that is turn controls the fan motor (20) and thus the pressure of air delivered by the blower (10). The blower (10) is coupled to a subject's mask (ii) by a conduit (12). The invention seeks to address the following goals: while the subject is awake and making substantial efforts the delivered assistance should be closely matched in phase with the subject's efforts; the machine should automatically adjust the degree of assistance to maintain at least a specified minimum ventilation without relying on the integrity of the subject's chemoreflexes; and it should continue to work correctly in the presence of large leaks.

18 Claims, 20 Drawing Sheets

Time since mask off-on transition

METHOD FOR PROVIDING VENTILATORY ASSISTANCE IN A SPONTANEOUSLY BREATHING SUBJECT

This application is a division of my prior copending application Ser. No. 08/935,785 filed Sep. 23, 1997 and correspondingly thereto claims the benefit of the priority of two earlier filed foreign applications, namely, Australian application No. PO2474 filed Sep. 23,1996, and International application No. PCT/AU97/00517 filed Aug. 14, 1997 and designating the United States of America.

FIELD OF THE INVENTION

The invention relates to methods and apparatus for the provision of ventilatory assistance matched to a subject's respiratory need. The ventilatory assistance can be for a subject who is either spontaneously or non-spontaneously breathing, or moves between these breathing states. The invention is especially suitable for, but not limited to, spontaneously breathing human subjects requiring longterm ventilatory assistance, particularly during sleep.

BACKGROUND OF THE INVENTION

Subjects with severe lung disease, chest wall disease, neuromuscular disease, or diseases of respiratory control may require in-hospital mechanical ventilatory assistance, followed by longterm home mechanical ventilatory assistance, particularly during sleep. The ventilator delivers air or air enriched with oxygen to the subject, via an interface such as a nosemask, at a pressure that is higher during inspiration and lower during expiration.

In the awake state, and while waiting to go to sleep, the subject's ventilatory pattern is variable in rate and depth. Most known ventilatory devices do not accurately match the amplitude and phase of mask pressure to the subject's spontaneous efforts, leading to discomfort or panic. Larger amounts of asynchrony also reduce the efficiency of the device. During sleep, there are changes in the neural control of breathing as well as the mechanics of the subject's airways, respiratory muscles and chest wall, leading to a need for substantially increased ventilatory support. Therefore, unless the device can automatically adjust the degree of support the amplitude of delivered pressure will either be inadequate during sleep, or must be excessive in the awake state. This is particularly important in subjects with abnormalities of respiratory control, for example central hypoventilation syndromes, such as Obesity Hypoventilation Syndrome, where these is inadequate chemoreceptor drive, or Cheyne Stokes breathing such as in patients with severe cardiac failure or after a stroke, where there is excessive or unstable chemoreceptor drive.

Furthermore, during steep these are inevitably large leaks between mask and subject, or at the subject's mouth if this is left free. Such leaks worsen the error in matching the phase and magnitude of the machine's effort to the subject's needs, and, in the case of mouth leak, reduce the effectiveness of the ventilatory support.

Ideally a ventilatory assistance device should simultaneously address the following goals:

(i) While the subject in awake and making substantial ventilatory efforts, the delivered assistance should be closely matched in phase with the patient's efforts.

(ii) The machine should automatically adjust the degree of assistance to maintain at least a specified minimum ventilation, without relying on the integrity of the subject's chemoreflexes.

(iii) It should continue to work correctly in the presence of large leaks.

Most simple home ventilators either deliver a fixed volume, or cycle between two fixed pressures. They do so either at a fixed rate, or are triggered by the patient's spontaneous efforts, or both. All such simple devices fail to meet goal (ii) of adjusting the degree of assistance to maintain at least a given ventilation. They also largely fail to meet goal (i) of closely matching the subjects respiratory phase: timed devices make no attempt to synchronize with the subject's efforts, triggered devices attempt to synchronize the start and end of the breath with the subject's efforts, but make no attempt to tailor the instantaneous pressure during a breath to the subject's efforts. Furthermore, the triggering tends to fail in the presence of leaks, thus failing goal (iii).

The broad family of servo-ventilators known for at least 20 years measure ventilation and adjust the degree of assistance to maintain ventilation at or above a specified level, thus meeting goal (ii), but they still fail to meet goal (i) of closely matching the phase of the subject's spontaneous efforts, for the reasons given above. No attempt is made to meet goal (iii).

Proportional assistist ventilation (PAV), as taught by Dr Magdy Younes, for example in *Principles and Practice of Mechanical Ventilation*, chapter 15, aims to tailor the pressure vs time profile within a breath to partially or completely unload the subject's resistive and elastic work, while minimizing the airway pressure required to achieve the desired ventilation. During the respiratory half-cycle, the administered pressure takes the form:

$$P(t) = P_0 + R \cdot f_{RESP}(t) + E, V(t)$$

where R is a percentage of the resistance of the airway, $f_{RESP}(t)$ is the instantaneous respiratory airflow at time t, E is a percentage of the elastance of lung and chest wall, and V(t) is the volume inspired since the start of inspiration to the present moment. During the expiratory half-cycle, V(t) is taken as zero, to produce passive expiration.

An advantage of proportional assist ventilation during spontaneous breathing is that the degree of assistance is automatically adjusted to suit the subject's immediate needs and their pattern of breathing, and is therefore comfortable in the spontaneously breathing subject. However, there are at lease two important disadvantages. Firstly, V(t) is calculated as the integral of flow with respect to time since the start of inspiration. A disadvantage of calculating V(t) in this way is that, in the presence of leaks, the integral of the flow through the leak will be included in V(t), resulting in an overestimation of V(t), in turn resulting in a runaway increase in the administered pressure. This can be distressing to the subject. Secondly, PAV relies on the subject's chemoreceptor reflexes to monitor the composition of the arterial blood, and thereby set the level of spontaneous effort. The PAV device then amplifies this spontaneous effort. In subjects with abnormal chemoreceptor reflexes, the spontaneous efforts may either cease entirely, or become unrelated to the composition of the arterial blood, and amplification of these efforts will yield inadequate ventilation. In patients with existing Cheyne Stokes breathing during sleep, PAV will by design amplify the subject's waxing and waning breathing efforts, and actually make matters worse by exaggerating the disturbance. Thus PAV substantially meets goal (i) of providing assistance in phase with the subject's spontaneous ventilation, but cannot meet goal (ii) of adjusting the depth of assistance if the subject has inadequate chemoreflexes, and does not satisfactorily meet goal (iii).

Thus there are known devices that meet each of the above goals, but there is no device that meets all the goals simultaneously. Additionally, it is desirable to provide improvements over the prior art directed to any one of the stated goals, Therefore, the present invention seeks to achieve, at least partially, one or more of the following:
(i) to match the phase and degree of assistance to the subject's spontaneous efforts when ventilation is well above a target ventilation,
(ii) to automatically adjust the degree of assistance to maintain at least a specified minimum average ventilation without relying on the integrity of the subject's chemoreflexes and to damp out instabilities in the spontaneous ventilatory efforts, such as Cheyne Stokes breathing.
(iii) to provide some immunity to the efforts of sudden leaks.

DISCLOSURE OF THE INVENTION

In what follows, a fuzzy membership function is taken as retaining a value between zero and unity, fuzzy intersection A AND B is the smaller of A and B, fuzzy union A OR B is the larger of A and B, and fuzzy negation NOT A is 1−A.

The invention discloses the determination of the instantaneous phase in the respiratory cycle as a continuous variable.

The invention further discloses a method for calculating the instantaneous phase in the respiratory cycle including at least the steps of determining that if the instantaneous airflow is small and increasing fast, trim it is close to start of inspiration, if the instantaneous airflow is large and steady, then it is close to mid-inspiration, if the instantaneous airflow in small and decreasing fast, then it a close to mid-expiration, if the instantaneous airflow is zero and steady, then it is during an end-expiratory pause, and airflow conditions intermediate between the above are associated with correspondingly intermediate phases.

The invention further discloses a method for determining the instantaneous phase in the respiratory cycle as a continuous variable from 0 to 1 revolution, the method comprising the steps of:
selecting at least two identifiable features $F_N$ of a prototype flow-vs-time waveform f(t) similar to an expected respiratory flow-vs-time waveform, and for each said feature:
determining by inspection the phase $\phi_N$ in the respiratory cycle for said feature, assigning a weight $W_N$ to said phase,
defining a "magnitude" fuzzy set $M_N$ whose membership function is a function of respiratory airflow, and a "rate of change" fuzzy set $C_N$, whose membership function is a function of the time derivative of respiratory airflow, chosen such that the fuzzy intersection $M_N$ AND $C_N$ will be larger for points on the generalized prototype respiratory waveform whose phase is closer to the said feature $F_N$ than for points closer to all other selected features,
setting the fuzzy inference rule $R_N$ for the selected feature $F_N$ to be: If flow is $M_N$ and rate of change of flow in $C_N$ then phase=$\phi_N$, with weight $W_N$.
measuring leak-corrected respiratory airflow,
for each feature $F_N$ calculating fuzzy membership to fuzzy acts $M_N$ and $C_N$,
for each feature $F_N$ applying fuzzy inference rule $R_N$ to determine the fuzzy extent $Y_N=M_N$ AND $C_N$ to which the phase is $\phi_N$, and
applying a defuzzification procedure using $Y_N$ at phases $\phi_N$ and weights $W_N$ to determine the instantaneous phase $\phi$.

Preferably, the identifiable features include zero crossings, peaks, inflection points or plateaus of the prototype flow-vs-time waveform. Furthermore, said weights can be unity, or chosen to reflect the anticipated reliability of deduction of the particular feature.

The invention further discloses a method for calculating instantaneous phase in the respiratory cycle as a continuous variable, as described above, in which the step of calculating respiratory airflow includes a low pass filtering step to reduce non-respiratory noise, in which the time constant of the low pass filter is an increasing function of an estimate of the length of the respiratory cycle.

The invention further discloses a method for measuring the instantaneous phase in the respiratory cycle as a continuous variable as described above, in which the defuzzification step includes a correction for any phase delay introduced in the step of low pass filtering respiratory airflow.

The invention further discloses a method for measuring the average respiratory rate, comprising the steps of:
measuring leak-corrected respiratory airflow,
from the respiratory airflow, calculating the instantaneous phase $\phi$ in the respiratory cycle as a continuous variable from 0 to 1 revolution, calculating the instantaneous rate of change of phase d$\phi$/dt, and
calculating the average respiratory rate by low pass filtering said instantaneous rate of change of phase d$\phi$/dt.

Preferably, the instantaneous phase is calculated by the methods described above.

The invention further discloses a method for providing ventilatory assistance in a spontaneously breathing subject, comprising the steps, performed at repeated sampling intervals, of:
ascribing a desired waveform template function $\Pi(\phi)$, with domain 0 to 1 revolution and range 0 to 1,
calculating the instantaneous phase $\phi$ in the respiratory cycle as a continuous variable from 0 to 1 revolution,
selecting a desired pressure modulation amplitude A,
calculating a desired instantaneous delivery pressure as an end expiratory pressure plus the desired pressure modulation amplitude A multiplied by the value of the waveform template function $\Pi(\phi)$ at the said calculated phase $\phi$ and
setting delivered pressure to subject to the desired delivery pressure.

The invention further discloses a method for providing ventilatory assistance in a spontaneously breathing subject as described above, in which the step of selecting a desired pressure modulation amplitude is a fixed amplitude.

The invention further discloses a method for providing ventilatory assistance in a spontaneously breathing subject as described above, in which the step of selecting a desired pressure modulation amplitude in which said amplitude is equal to an elastance multiplied by an estimate of the subject's tidal volume.

The invention further discloses a method for providing ventilatory assistance in a spontaneously breathing subject as described above, in which the step of selecting a desired pressure modulation amplitude comprises the substeps of:
specifying a typical respiratory rate giving a typical cycle time,
specifying a preset pressure modulation amplitude to apply at said typical respiratory rate, calculating the observed respiratory rate giving an observed cycle time, and calculating the desired amplitude of pressure modulation as said preset pressure modulation amplitude multiplied by said observed cycle time divided by the said specified cycle time.

The invention further discloses a method for providing ventilatory assistance in a spontaneously breathing subject, including at least the step of determining the extent that the subject is adequately ventilated, to said extent the phase in the respiratory cycle is determined from the subject's respiratory airflow, but to the extent that the subject's ventilation is inadequate, the phase in the respiratory cycle is assumed to increase at a pre-set rate, and setting mask pressure as function of said phase.

The invention further discloses a method for providing ventilatory assistance in a spontaneously breathing subject, comprising the steps of: measuring respiratory airflow, determining the extent to which the instantaneous phase in the respiratory cycle can be determined from said airflow, to said extent determining said phase from said airflow but to the extent that the phase in the respiratory cycle cannot be accurately determined, the phase is assumed to increase at a preset rate, and delivering pressure as a function of said phase.

The invention further discloses a method for calculating the instantaneous inspired volume of a subject, operable substantially without run-away under conditions of suddenly changing leak, the method comprising the steps of:

determining respiratory airflow approximately corrected for leak, calculating an index J varying from 0 to 1 equal to the fuzzy extent to which said corrected respiratory airflow is large positive for longer than expected, or large negative for longer than expected, identifying the start of inspiration, and calculating the instantaneous inspired volume as the integral of said corrected respiratory airflow multiplied by the fuzzy negation of said index J with respect to time, from start of inspiration.

The invention further discloses a method "A" for providing ventilatory assistance in a spontaneously breathing subject, the method comprising the steps, performed at repeated sampling intervals, of:

determining respiratory airflow approximately corrected for leak, calculating an index J varying from 0 to 1 equal to the fuzzy extent to which said respiratory airflow is large positive for longer than expected, or large negative for longer than expected, calculating a modified airflow equal to said respiratory airflow multiplied by the fuzzy negation of said index J, identifying the phase in the respiratory cycle, calculating the instantaneous inspired volume as the integral of said modified airflow with respect to time, with the integral held at zero during the expiratory portion of the respiratory cycle, calculating a desired instantaneous delivery pressure as a function at least of the said instantaneous inspired volume, and setting delivered pressure to subject to the desired delivery pressure.

The invention further discloses a method "B" for providing ventilatory assistance in a spontaneously breathing subject, comprising the steps of:

determining respiratory airflow approximately corrected for leak, calculating an index J varying from 0 to 1 equal to the fuzzy extent to which the respiratory airflow is large positive for longer than expected, or large negative for longer than expected, identifying the phase in the respiratory cycle, calculating a modified respiratory airflow equal to the respiratory airflow multiplied by the fuzzy negation of said index J, calculating the instantaneous inspired volume as the integral of the modified airflow with respect to time, with the integral held at zero during the expiratory portion of the respiratory cycle, calculating the desired instantaneous delivery pressure as an expiratory pressure plus a resistance multiplied by the instantaneous respiratory airflow plus a nonlinear resistance multiplied by the respiratory airflow multiplied by the absolute value of the respiratory airflow plus an elastance multiplied by the said adjusted instantaneous inspired volume, and setting delivered pressure to subject to the desired delivery pressure.

The invention yet further discloses a method "C" for providing assisted ventilation to match the subject's need, comprising the steps of:

describing a desired waveform template function $\Pi(\phi)$ with domain 0 to 1 revolution and range 0 to 1, determining respiratory airflow approximately corrected for leak, calculating an index J varying from 0 to 1 equal to the fuzzy extent to which the respiratory airflow is large positive for longer than expected, or large negative for longer than expected, calculating $J_{PEAK}$ equal to the recent peak of the index J, calculating the instantaneous phase in the respiratory cycle, calculating a desired amplitude of pressure modulation, chosen to servo-control the degree of ventilation to at least exceed a specified ventilation, calculating a desired delivery pressure as an end expiratory pressure plus the calculated pressure modulation amplitude A multiplied by the value of the waveform template function $\Pi(\phi)$ at the said calculated phase $\phi$, and setting delivered pressure to subject to said desired instantaneous delivered pressure.

The invention yet further discloses a method for providing assisted ventilation to match the subject's need, as described above, in which the step of calculating a desired amplitude of pressure modulation, chosen to servo-control the degree of ventilation to at least exceed a specified ventilation, comprises the steps of:

calculating a target airflow equal to twice the target ventilation divided by the target respiratory rate, deriving an error term equal to the absolute value of the instantaneous low pass filtered respiratory airflow minus the target airflow, and calculating the amplitude of pressure modulation as the integral of the error term multiplied by a gain, with the integral clipped to lie between zero and a maximum.

The invention yet further discloses a method for providing assisted ventilation to match the subject's need, as described above, in which the step of calculating a desired amplitude of pressure modulation, chosen to servo-control the degree of ventilation to at least exceed a specified ventilation, comprises the following steps:

calculating a target airflow equal to twice the target ventilation divided by the target respiratory rate, deriving an error term canal to the absolute value of the instantaneous low pass filtered respiratory airflow minus the target airflow, calculating an uncorrected amplitude of pressure modulation as the integral of the error term multiplied by a gain, with the integral clipped to lie between zero and a maximum, calculating the recent average of said amplitude as the low pass filtered amplitude, with a time constant of several times the length of a respiratory cycle, and setting the actual amplitude of pressure modulation to equal the said low pass filtered amplitude multiplied by the recent peak jamming index $J_{PEAK}$ plus the uncorrected amplitude multiplied by the fuzzy negation of $J_{PEAK}$.

The invention yet further discloses a method for providing assisted ventilation to match the subject's need, and with particular application to subjects with varying respiratory mechanics, insufficient respiratory drive, abnormal chemoreceptor reflexes, hypoventilation syndromes, or Cheyne Stokes breathing, combined with the advantages of proportional assist ventilation adjusted for sudden changes in leak, comprising the steps, performed at repeated sampling intervals, of:

calculating the instantaneous mask pressure as described for methods "A" or "B" above, calculating the instantaneous mask pressure as described for method "C" above, calculating a weighted average of the above two pressures, and setting the mask pressure to the said weighted average.

The invention yet further discloses apparatus to give effect to each one of the methods defined, including one or more transducers to measure flow and/or pressure. processor means to perform calculations and procedures, flow generators for the supply of breathable gas at a pressure above atmospheric pressure and gas delivery means to deliver the breathable gas to a subject's airways.

The apparatus can include ventilators, ventilatory assist devices, and CPAP devices including constant level, bi-level or autosetting level devices.

It is to be understood that while the algorithms embodying the invention are explained in terms of fuzzy logic, approximations to these algorithms can be constructed without the use of the fuzzy logic formalism.

BRIEF DESCRIPTION OF THE DRAWINGS

A number of embodiments will now be described with reference to the accompanying drawings in which:

FIG. 21 shows that a short central apnea (b) is permitted when effort ceases at point (c) after a preceding deep breath (a);

FIG. 22 shows that a central apnea is not permitted when effort ceases at arrow (a) without a preceding deep breath;

FIG. 23 is recorded with servo gain set high, and shows that a central apnea is no longer permitted when effort ceases at arrow (a) despite preceding deep breathing;

FIG. 24 shows automatically increasing end-inspiratory pressure as the subject makes voluntarily deeper inspiratory efforts;

FIG. 25 is recorded with a somewhat more square waveform selected, and shows automatically increasing pressure support when the subject voluntarily attempts to resist by stiffening the chest wall at point (a);

FIG. 26 shows that with sudden onset of a sever 1.4 L/sec leak at (a), the flow signal returns to baseline (b) within the span of a single breath, and pressure continues to cycle correctly throughout.

DESCRIPTION OF PREFERRED EMBODIMENTS

The two embodiments to be described are ventilators that operate in a manner that seeks to simultaneously achieve the three goals stated above.

First Embodiment

Figure 1A:
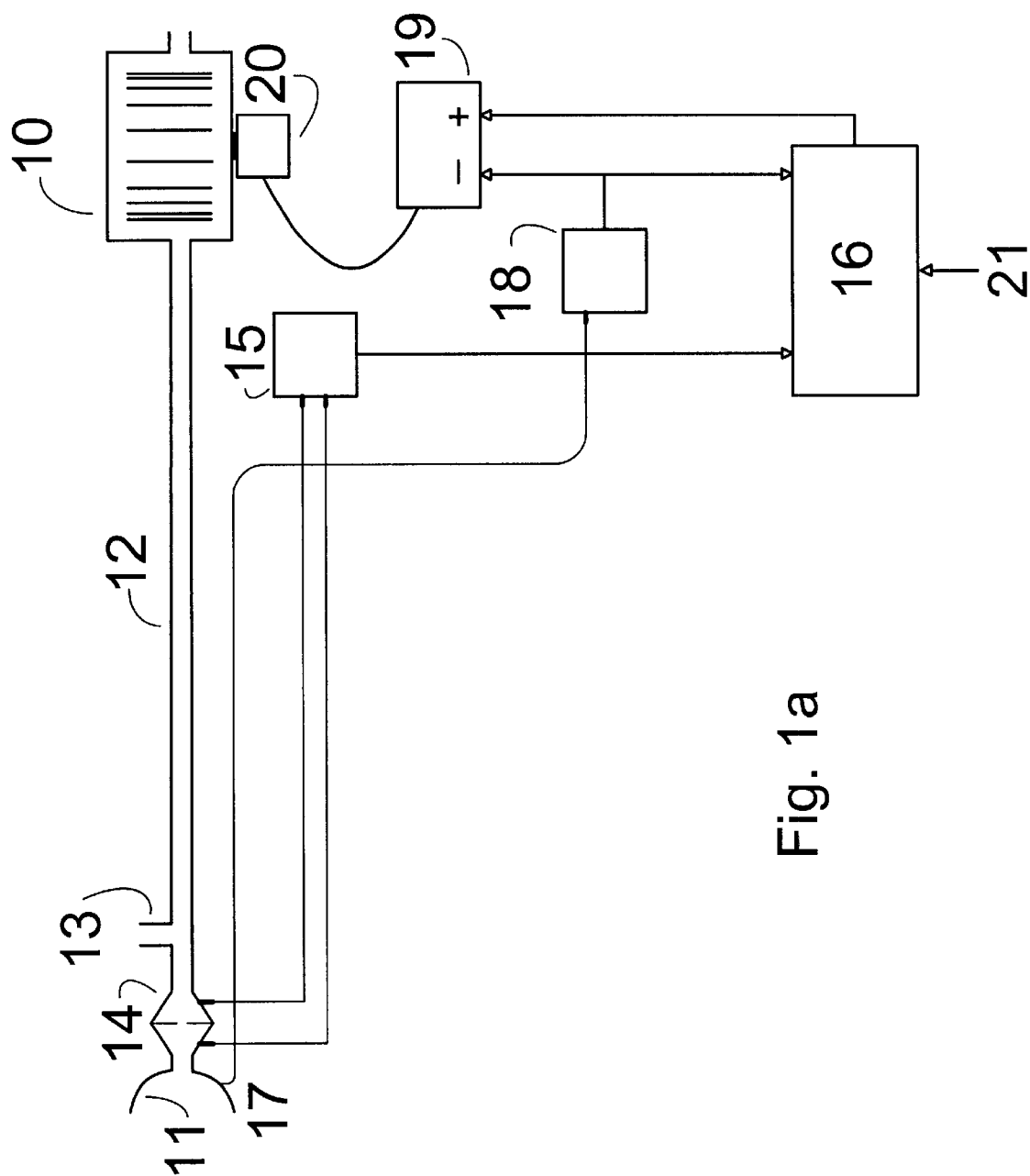
FIGS. 1a and 1b show apparatus for first and second embodiments of the invention respectively.

Apparatus to give effort to a first embodiment of the apparatus is shown in FIG. 1a. A blower 10 supplies a breathable gas to mask 11 in communication with the subject's airway via a delivery tube 12 and exhausted via a exhaust diffuser 13. Airflow to the mask 11 is measured using a pneumotachograph 14 and a differential pressure transducer 15. The mask flow signal from the transducer 15 is then sampled by a microprocessor 16. Mask pressure is measured at the port 17 using a pressure transducer 18. The pressure signal from the transducer 18 is then sampled by the microprocessor 16. The microprocessor 16 sends an instantaneous mask pressure request signal to the servo 19, which compares said pressure request signal with actual pressure signal from the transducer 18 to the control fan motor 20. The microprocessor settings can be adjusted via a serial port 21.

It is to be understood that the mask could equally be replaced with a tracheotomy tube, endotracheal tube, nasal pillows, or other means of making a sealed connection between the air delivery means and the subject's airway.

The microprocessor 16 is programmed to perform the following steps, to be considered in conjunction with Tables 1 and 2.

TABLE 1

Fuzzy Inference Rules for a first embodiment

| N | Fuzzy Interference Rule | | | Fuzzy Phase |
|---|---|---|---|---|
| 1 | if size is Zero | and rate of change is | Increasing | then phase is Start Inspiration |
| 2 | if size is Small Positive | and rate of change is | Increasing Slowly | then phase is Early Inspiration |
| 3 | if size is Large Positive | and rate of change is | Steady | then passe is Peak Inspiration |
| 4 | if size is Small Positive | and rate of change is | Decreasing Slowly | then phase is Late Inspiration |
| 5 | if size is Zero | and rate of change is | Decreasing Fast | then phase is Start Expiration |
| 6 | if size is Small Negative | and rate of change is | Decreasing Slowly | then phase is Early Expiration |
| 7 | if size is Large Negative | and rate of change is | Steady | then phase is Peak Expiration |
| 8 | if size is Small Negative | and rate of change is | Increasing Slowly | then phase is Late Expiration |
| 9 | if size is Zero | and rate of change is | Steady | then phase is Expiratory Pause |
| 10 | always | | | phase is Unchanged |

TABLE 2

Association of phases with fuzzy rules for a first embodiment.

| N | Phase | $\Phi_N$ |
|---|---|---|
| 1 | Start Inspiration | 0.0 |
| 2 | Early Inspiration | values |
| 3 | Peak Inspiration | intermediate between |
| 4 | Late Inspiration | 0.0 and 0.5 |
| 5 | Start Expiration | 0.50 |
| 6 | Early Expiration | values |
| 7 | Peak Expiration | intermediate between |
| 8 | Late Expiration | 0.5 and 1.0 |
| 9 | Expiratory Pause | |
| 10 | Unchanged | $\Phi$ |

Figure 2:
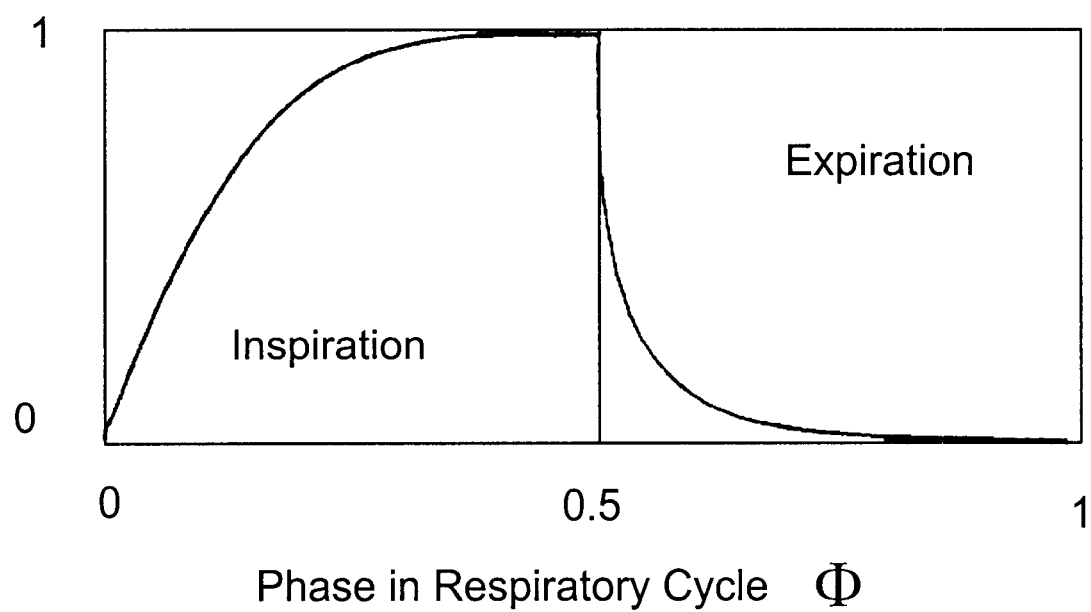
FIG. 2 is a pressure waveform function $\Pi(\phi)$ used in the calculation of the desired instantaneous delivery pressure as a function of the instantaneous phase $\phi$ in the respiratory cycle for a first embodiment of the invention.

1. Set desired target values for the duration of inspiration $TI_{TGT}$, duration of expiration $TE_{TGT}$, and minute ventilation $V_{TGT}$. Choose suitable constants $P_0$ and $A_{STD}$ where $P_0$ is the desired end expiratory pressure, and $A_{STD}$ is the desired increase in pressure above $P_0$ at end inspiration for a breath of duration $TT_{TGT}=TI_{TGT}+TE_{TGT}$.
2. Choose a suitable pressure waveform function $\Pi(\phi)$ such as that shown in FIG. 2, such chat the desired delivery pressure at phase $\phi$ will be given by:

$$P=P_0+A\Pi(\phi)$$

where the amplitude A equals the difference between the end inspiratory pressure and end expiratory pressure. However, other waveforms may be suitable for subjects with particular heads.
3. Initialize the phase $\phi$ in the respiratory cycle to zero, and initialize the current estimates of actual inspiratory and expiratory duration TI and TE to $TI_{TGT}$ and $TE_{TGT}$ respectively.
4. Initialize the rate of change of phase during inspiration $\Delta\phi_I$ between sampling intervals of length T to:

$\Delta\phi_E += 0.5 \ T/TI_{TGT}$

5. Initialize the rate of change of phase during expiration $\Delta\phi_E$ to:

$\Delta\phi_E = 0.5 \ T/TE_{TGT}$

6. Measure the instantaneous respiratory airflow $f_{RESP}$.
7. Calculate the average total breath duration TT=TI+TE
8. Low pass filter the respiratory airflow with an adjustable time constant τf, where τf is a fixed small fraction of TT.
9. Calculate the instantaneous ventilation V, as half the absolute value of the respiratory airflow:

$V = 0.5 |f_{RESP}|$

10. From the target ventilation $V_{TGT}$ and the measured minute ventilation V, derive an error term $V_{ERR}$, such that large values of $V_{ERR}$ indicate inadequate ventilation:

$V_{ERR} = \int (V_{TGT} - V) dt$

11. Take $V_{BAR}$ as the result of low pass filtering V with a time constant $\tau V_{BAR}$ which is long compared with TT.
12. Calculate a normalized airflow $f_{NORM}$, where $f_{NORM} = f_{RESP}/V_{BAR}$.

Figure 3:
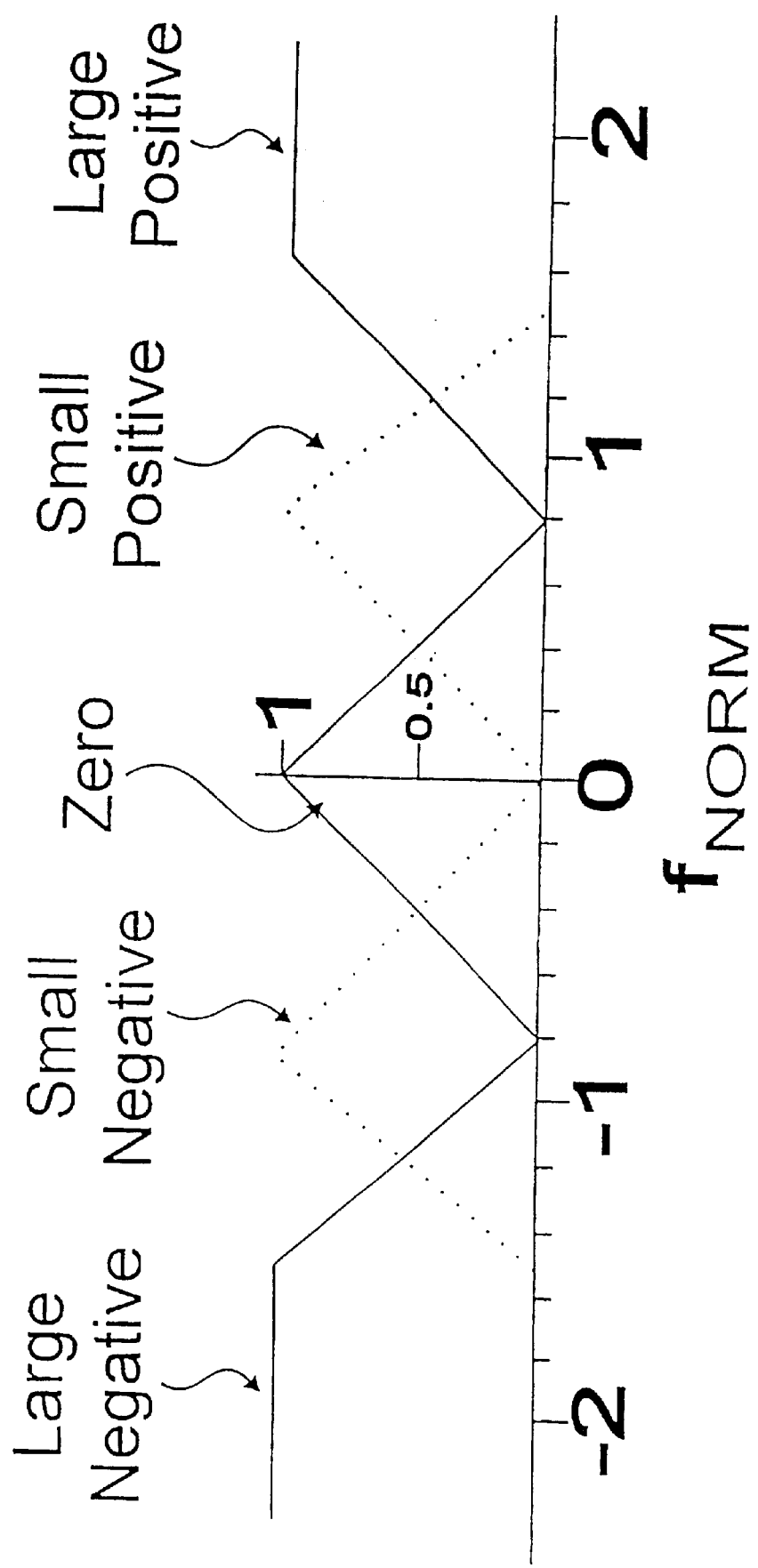
FIG. 3 shows fuzzy membership functions for calculating the degree of membership in each of five magnitude fuzzy sets ("large negative", "small negative", "zero", "small positive", and "large positive") from the normalized respiratory airflow according to the first embodiment of the invention.
Figure 4:
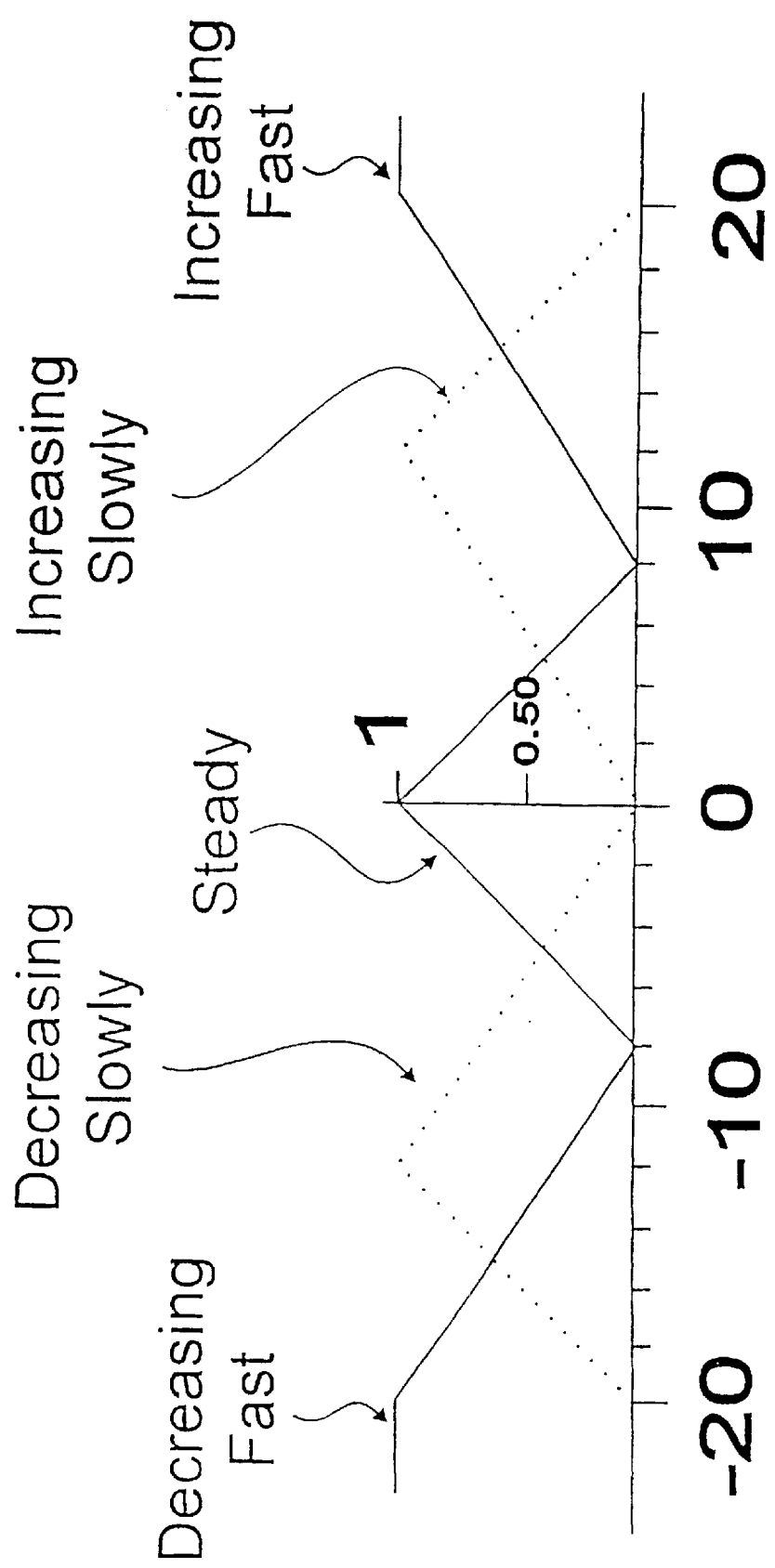
FIG. 4 shows fuzzy membership functions for calculating the degree of membership in each of five rate of change fuzzy sets ("rising fast", "rising slowly", "steady", "falling slowly", and "falling fast") from the normalized rate of change of airflow according to the first embodiment of the invention.

13. From $f_{NORM}$, calculate the degree of membership in each of the fuzzy sets whose membership functions are shown in FIG. 3.
14. Calculate a normalized rate of change $df_{NORM}/d\phi$ equal to $df_{NORM}/dt$ divided by the current estimate of the average respiratory cycle time TT.
15. From the normalized rate of change, calculate the degree of membership in each of the fuzzy sets shown in FIG. 4.
16. For each row N in Table 1, calculate the degree of membership $g_N$ in the fuzzy set shown in the column labelled Fuzzy Phase, by applying the fuzzy inference rules shown.
17. Associate with the result of each of the N rules a phase $\phi_N$ as shown in Table 2, noting that $\phi_{10}$ is the current phase $\phi$.
18. Increase each of the $\phi_N$ excepting $\phi_{10}$ by 0.89 τ/TT, to compensate for the previous law pass filtering step.
19. Calculate a new instantaneous phase $\phi_{INST}$ as the angle to the center of gravity of N unit masses at polar coordinates of radius $g_N$ and angle $\phi_n$ revolutions.
20. Calculate the smallest difference $\Delta\phi_{INST}$ between the phase estimated in the previous step and the current phase.

$\Delta\phi_{INST} = 1 - (\Delta\phi_{INST} - \phi) \ (\phi_{INST} - \phi > 0.5)$ $\Delta\phi_{INST} = \phi_{INST} - \phi + 1 \ (\phi_{INST} - \phi < -0.5)$ $\Delta\phi_{INST} = \phi_{INST} - \phi \ (\text{otherwise})$ 21. Derive a revised estimate $\Delta\phi_{REV}$ equal to a weighted mean of the value calculated in the previous step and the average value ($\Delta\phi_I$ or $\Delta\phi_E$ as appropriate).

$\Delta\phi = (1-W)\Delta\phi_I + W\Delta\phi_{INST} \ (0 < \phi 0.5)$ $\Delta\phi = (1-W)\Delta\phi_I + W\Delta\phi_{INST} \ (\text{otherwise})$ Smaller values of W will cause better tracking of phase if the subject is breathing regularly, and larger values will cause better tracking of phase if the subject is breathing irregularly.
22. Derive a blending fraction B, such that the blending fraction is unity if the subject's ventilation is well above $V_{TGT}$, zero if the subject is breathing near or below $V_{TGT}$, and increasing proportionally from zero to unity as the subject's ventilation increases through an intermediate range.
23. Calculate $\Delta\phi_{BLEND}$ influenced chiefly by $\Delta\phi$ calculated in step 21 from the subject's respiratory, activity if the subject's ventilation is well above $V_{TGT}$; influenced chiefly by the target respiratory duration if the subject is breathing near or below $V_{TGT}$; and proportionally between these two amounts if ventilation is in an intermediate range:

$\Delta\phi_{BLEND} = B\Delta\phi + 0.5 \ (1-B) \ TI_{TGT} \ (0 < \phi < 0.5)$ $\Delta\phi_{BLEND} = B\Delta\phi + 0.5 \ (1-B) \ TI_{TGT} \ (\text{otherwise})$ 24. Increment $\phi$ by $\Delta\phi_{BLEND}$
25. Update the average rate of change of phase ($\Delta\phi_I$ or $\Delta\phi_I = T/\tau_{VBAR}(\Delta\phi_{BLEND} - \Delta\phi_I) \ (0 < \phi < 0.5)$ $\Delta\phi_E = T/\tau_{VBAR}(\Delta\phi_{BLEND} - \Delta\phi_E) \ (\text{otherwise})$ 26. Recalculate the approximate duration of inspiration TI and expiration TE:

$TI = 0.5 \ T/\Delta\phi_I$ $TE = 0.5 \ T/\Delta\phi_E$

27. Calculate the desired mask pressure modulation amplitude $A_D$:

$A_D = A_{STD}/2 \ (TT < TT_{STD}/2)$ $A_D = 2 \cdot A_{STD} \ (TT > TT_{STD})$ $A_D = A_{STD} \cdot TT/TT_{STD} \ (\text{otherwise})$ 28. From the error term $V_{ERR}$, calculate an additional mask pressure modulation amplitude $A_E$:

$A_E = K \cdot V_{ERR} \ (\text{for } V_{ERR} > 0)$ $A_E = 0 \ (\text{otherwise})$ where larger values of K will produce a faster but less stable control of the degree of assistance, and smaller values of K will produce slower but more stable control of the degree of assistance.
29. Set the mask pressure $P_{MASK}$ to:

$P_{MASK} = P_0 + (A_D + A_E)\Pi(\phi)$

30. Wait for a sampling interval T, short compared with the duration of a respiratory cycle, and then continue at the step of measuring respiratory airflow.

Measurement of Respiratory Airflow

As follows from above, it is necessary to respiratory airflow, which is a standard procedure to one skilled in the art. In the absence of leak, respiratory airflow can be measured directly with a pneumotachograph placed between the mask and the exhaust. In the presence of a possible leak, one method disclosed in European Publication No 0 651 971 incorporated herein by cross-reference is to calculate the mean flow through the leak, and thence calculate the amount of modulation of the pneumotachograph flow signal due to modulation of the flow through the leak induced by changing mask pressure, using the following steps:

1. Measure the airflow at the mask $f_{MASK}$ using a pneumotachograph
2. Measure the pressure at the mask $P_{MASK}$ 3. Calculate the mean leak as the low pass filtered airflow, with a time constant long compared with a breath.
4. Calculate the mean mask pressure as the low pass filtered mask pressure, with a time constant tong compared with a breath.
5. Calculate the modulation of the flow through the leak as:

$\delta(\text{leak}) = 0.5$ times the mean leak times the inducing pressure, where the inducing pressure is $P_{MASK}$–mean mask pressure, Thence the instantaneous respiratory airflow can be calculated as:

$f_{RESP} = f_{MASK}$–mean leak–$\delta(\text{leak})$

A convenient extension as further disclosed in EP 0 651 971 (incorporated herein by cross-reference) is to measure airflow $f_{TURBINE}$ and pressure $P_{TURBINE}$ at the outlet of the turbine, and thence calculate $P_{MASK}$ and $f_{MASK}$ by allowing for the pressure drop down the air delivery hose, and the airflow lost via the exhaust:

1. $\Delta P_{HOSE} = K_1(F_{TURBINE}) - K_2(F_{TURBINE})^2$
2. $P_{MASK} = P_{TURBINE} - \Delta P_{HOSE}$
3. $F_{EXHAUST} = K3\sqrt{P_{MASK}}$
4. $F_{MASK} = F_{TURBINE} - F_{EXHAUST}$

ALTERNATIVE EMBODIMENT

The following embodiment is particularly applicable to subjects with varying respiratory mechanics, insufficient respiratory drive, abnormal chemoreceptor reflexes, hypoventilation syndromes, or Cheyne Stokes breathing, or to subjects with abnormalities of the upper or lower airways, lungs, chest wall, or neuromuscular system.

Many patients with severe lung disease cannot easily be treated using a smooth physiological pressure waveform, because the peak pressure required is unacceptably high, or unachievable with for example a nose-mask. Such patients may prefer a square pressure waveform, in which pressure rises explosively fast at the moment of commencement of respiratory effort. This may be particularly important in patients with high intrinsic PEEP, in which it is not practicable to overcome the intrinsic PEEP by the use of high levels of extrinsic PEEP or CPAP, due to the risk of hyperinflation. In such subjects, any delay in triggering is perceived as very distressing, because of the enormous mis-match between expected and observed support. Smooth waveforms exaggerate the perceived delay, because of the time taken for the administered pressure to exceed the intrinsic PEEP. This embodiment permits the use of waveforms varying continuously from square (suitable for patients with for example severe lung or chest wall disease or high intrinsic PEEP) to very smooth, suitable for patients with normal lungs and chest wall, but abnormal respiratory control, or neuromuscular abnormalities. This waveform is combined either with or without elements of proportional assist ventilation (corrected for sudden changes in leak), with servo-control of the minute ventilation to equal or exceed a target ventilation. The latter servo-control has an adjustable gain, so that subjects with for example Cheyne Stokes breathing can be treated using a very high servo gain to over-ride their own waxing and waning patterns; subjects with various central hypoventilation syndromes can be treated with a low servo gain, so that shop central apneas are permitted, for example to cough, clear the throat, talk, or roil over in bed, but only if they follow a previous period of high ventilation; and normal subjects are treated with an intermediate gain.

Restating the about in other words:

The integral gain of the servo-control of the degree of assistance is adjustable from very fast (0.3 cmH$_2$O/L/sec/sec) to very slow. Patients with Cheyne-Stokes breathing have a very high ventilatory control loop gain, but a long control loop delay, leading to hunting. By setting the loop gain even higher, the patient's controller is stabilized. This prevents the extreme breathlessness that normally occurs during each cycle of Cheyne-Stokes breathing, and this is very reassuring to the patient. It is impossible for them to have a central apnea. Conversely, subjects with obesity-hypoventilation syndrome have low or zero loop gain. They will not feel breathless during a central apnea. However, they have much mucus and need to cough, and are also often very fidgety, needing to roll about in bed. This requires that they have central apneas which the machine does not attempt to treat. By setting the loop gain very low, the patient is permitted to take a couple of deep breaths and then have a moderate-length central apnea while coughing rolling over, etc, but prolonged sustained apneas or hypopneas are prevented.

Sudden changes in leakage flow are detected and handled using a fuzzy logic algorithm. The principle of the algorithm is that the leak filter time constant is reduced dynamically to the fuzzy extent that the apparent respiratory airflow is a long way from zero for a long time compared with the patient's expected respiratory cycle length.

Rather than simply triggering between two states (IPAP, EPAP), the device uses a fuzzy logic algorithm to estimate the position in the respiratory cycle as a continuous variable. The algorithm permits the smooth pressure waveform to adjust it's rise time automatically to the patient's instantaneous respiratory pattern.

The fuzzy phase detection algorithm under normal conditions closely tracks the patient's breathing. To the extent that there is a high or suddenly changing leak, or the patient's ventilation is low, the rate of change of phase (respiratory rate) smoothly reverts to the specified target respiratory rate. Longer or deeper hypopneas are permitted to the extent that ventilation is on average adequate. To the extent that the servo gain is set high to prevent Cheyne Stokes breathing, shorter and shallower pauses are permitted.

Airflow filtering uses an adaptive filter, which shortens it's time constant if the subject is breathing rapidly, to give very fast response times, and lengthens if the subject is breathing slowly, to help eliminate cardiogenic artifact.

The fuzzy changing leak detection algorithm, the fuzzy phase detection algorithm with its differential handling of brief expiratory pauses, and handling of changing leak, together with the smooth waveform severally and cooperatively make the system relatively immune to the effects of sudden leaks.

By suitably setting various parameters, the system can operate in CPAP, bilevel spontaneous, bilevel timed, proportional assist ventilation, volume cycled ventilation, and volume cycled servo-ventilation, and therefore all these modes are subsets of the present embodiment. However, the present embodiment permits states of operation that can not be achieved by any of the above states, and is therefore distinct from them.

Notes

Note 1: in this second embodiment, the names and symbols used for various quantities may be different to those used in the fast embodiment.

Note 2: The term "swing" is used to refer to the difference between desired instantaneous pressure at end inspiration and the desired instantaneous pressure at end expiration.

Note 3: A fuzzy membership function is taken as returning a value between zero for complete nonmembership and unity for complete membership. Fuzzy intersection A AND B is the lesser of A and B, fuzzy union A OR B is the larger of A and B, and fuzzy negation NOT A is 1−A.

Note 4: root(x) is the square root of x, abs(x) is the absolute value of x, sing(x) is −1 if x is negative, and +1 otherwise. An asterisk (*) is used to explicitly indicate multiplication where this might not be obvious from context.

Apparatus

Figure 1B:
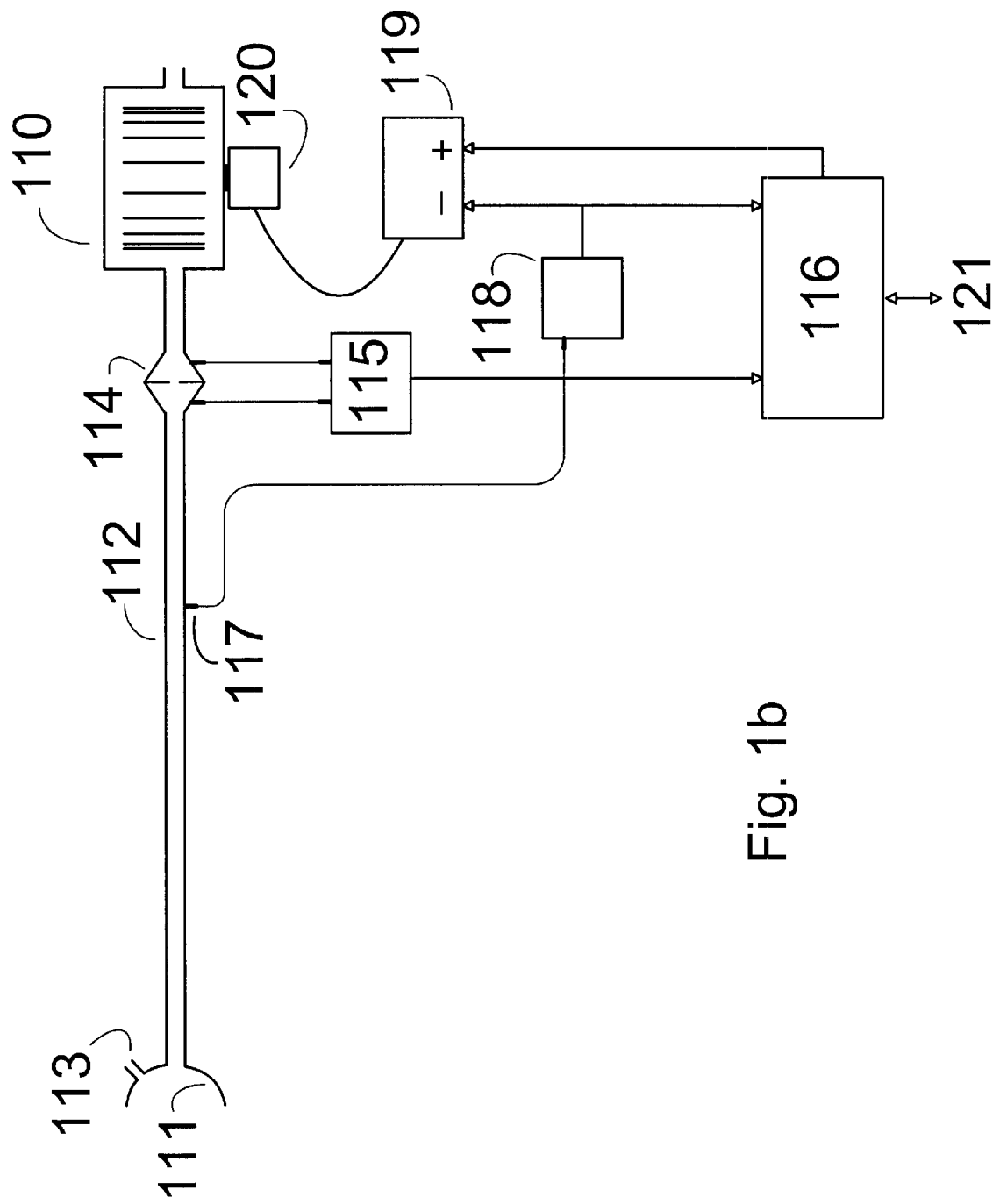

The apparatus for the second embodiment is shown in FIG. 1b. The blower 110 delivers air under pressure to the mask 111 via the air delivery hose 112. Exhaled air is exhausted via the exhaust 113 in the mask 111. The pneumotachograph 114 and a differential pressure transducer 115 measure the airflow in the nose 112. The flow signal is delivered to the microprocessor 116. Pressure at any convenient point 117 along the nose 112 is measured using a breathing transducer 118. The output from the pressure transducer 118 is delivered to the microcontroller 116 and also to a motor servo 114. The microprocessor 116 supplies the motor servo 119 with a pressure request signal, which is then compared with the signal from the pressure transducer 118 to control the blower motor 120. User configurable parameters are loaded into the microprocessor 116 via a communications port 121, and the computed mask pressure and flow can if desired be output via the communications port 121.

Initialization

The following user adjustable parameters are specified and stored:

| | |
|---|---|
| max permissible pressure | maximum permissible mask pressure |
| max swing | maximum permissible difference between end inspiratory pressure and end expiratory pressure. |
| min swing | minimum permissible difference between end inspiratory pressure and end expiratory pressure. |
| epap | end expiratory pressure |
| min permissible pressure | minimum permissible mask pressure |
| target ventilation | minute ventilation is sevo-controlled to equal or exceed this quantity |
| target frequency | Expected respiratory rate. If the patient is achieving no respiratory airflow, the pressure will cycle at this frequency. |
| target duty cycle | Expected ratio of inspiratory time to cycle time. If the patient is achieving no respiratory airflow, the pressure will follow this duty cycle. |
| linear resistance and quad resistance | resistive unloading = linear * f + quad_resistance * f² sign(f), where f is the respiratory airflow. where sign(x) = −1 for x < 0, +1 otherwise |
| elastance | Unload at least this much elastance |
| servo gain | gain for servo-control of minute ventilation to at least exceed target ventilation. |
| waveform time constant | Elastic unloading waveform time constant as a fraction of inspiratory duration. (0.0 = square wave) |
| hose resistance | ΔP from pressure sensing port to inside mask = hose resistance times the square of the flow in the intervening tubing. |
| diffuser conductance | Flow through the mask exhaust port = diffuser conductance * root mask pressure |

At initialization, the following are calculated from the about user-specified settings:

The expected duration of a respiratory cycle, of an inspiration, of an expiration are set respectively to:

STD $T_{TOT}$=60/target respiratory rate

STD $T_I$=STD $T_{TOT}$*target duty cycle

STD $T_E$=STD $T_{TOT}$−STD $T_I$

The standard rates of change of phase (revolutions per sec) during inspiration and expiration are set respectively to:

STD $d\phi_I$=0.5/STD $T_I$

STD $d\phi_E$=0.5/STD $T_E$

The instantaneous elastic support at any phase $\phi$ in the respiratory cycle is given by:

$PEL(\phi)$=swing*$\Pi(\phi)$ where swing is the pressure at end inspiration minus the pressure at end expiration, $\Pi(\phi)=e^{-2}\tau\phi$ during inspiration, $e^{-4}\tau(\phi-0.5)$ during expiration and τ is the user-selectable waveform time constant.

Figure 5:
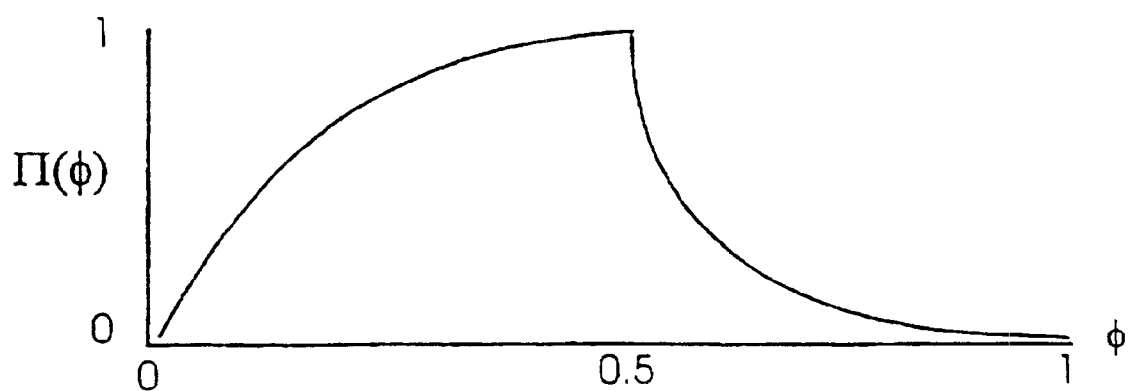
FIG. 5 is a pressure waveform function $\Pi(\phi)$ used in the calculation of the desired instantaneous delivery pressure as a function of the instantaneous phase $\phi$ is the respiratory cycle for a second embodiment of the invention.

If τ=0, then $\Pi(\phi)$ is a square wave. The maximum implemented value for τ=0.3, producing a waveform approximately as shown in FIG. 5.

The mean value of $\Pi(\phi)$ is calculated as follows:

$$\Pi_{BAR} = 0.5 \int_0^{.05} \Pi(\phi) d\phi$$

Operations Performed every 20 Milliseconds

The following is an overview of routine processing done at 50 Hz:

measure flow at flow sensor and pressure at pressure sensing port calculate mask pressure and flow from sensor pressure and flow calculate conductance of mask leak calculate instantaneous airflow through leak calculate respiratory airflow and low pass filtered respiratory airflow calculate mask on-off status and lead-in calculate instantaneous and recent peak jamming calculate time constant for leak conductance calculations calculate phase in respiratory cycle update mean rates of change of phase for inspiration and expiration, lengths of inspiratory and expiratory times, and respiratory rate add hose pressure loss to EPAP pressure add resistive unloading calculate instantaneous elastic assistance required to servo-control ventilation estimate instantaneous elastic recoil pressure using various assumptions weight and combine estimates add servo pressure to yield desired sensor pressure servo-control motor speed to achieve desired sensor pressure The details of each step will now be explained.

Measurement of Flow and Pressure

Flow is measured at the outlet of the blower using a pneumotachograph and differential pressure transducer. Pressure is measured at any convenient point between the blower outlet and the mask. A humidifier and/or anti-bacterial filter may be inserted between the pressure sensing port and the blower. Flow and pressure are digitized at 50 Hz using an A/D converter.

Calculation of Mask Flow and Pressure

The pressure loss from pressure measuring point to mask is calculated from the flow at the blower and the (quadratic) resistance from measuring point to mask.

Hose pressure loss=sign(flow)*hose resistance*flow$^2$ where sign(x)=−1 for x<0, +1 otherwise. The mask pressure is then calculated by subtracting the hose pressure loss from the measured sensor pressure:

Mask pressure=sensor pressure−hose pressure loss

The flow through the mask exhaust diffuser is calculated from the known parabolic resistance of the diffuser holes, and the square root of the mask pressure:

diffuser flow=exhaust resistance*sign(mask pressure)* root(abs(mask pressure))

Finally, the mask flow is calculated:

mask flow=sensor flow−diffuser flow

The foregoing describes calculation of mask pressure and flow in the various treatment modes. In diagnostic mode, the patient is wearing only nasal cannulae, not a mask. The cannula is plugged into the pressure sensing port The nasal airflow is calculated from the pressure, after a linerization step, and the mask pressure is set to zero by definition.

Conductance of Leak

The conductance of the leak is calculated as follows:

root mask pressure=sign ($P_{MASK}$) $\sqrt{abs\ (P_{MASK})}$

LP mask airflow=loss pass filtered mask airflow

LP root mask pressure=low pass filtered root mask pressure conductance of leak=LP mask airflow/LP root mask pressure The time constant for the two low pass filtering steps is initialized to 10 seconds and adjusted dynamically thereafter (see below).

Instantaneous Flow Through Leak

The instantaneous flow through the leak is calculated from the instantaneous mask pressure and the conductance of the leak:

instantaneous leak=conductance of leak*root mask pressure

Respiratory Airflow

The respiratory airflow is the difference between the flow at the mask and the instantaneous leak:

respiratory airflow=mask flow−instantaneous leak

Low Pass Filtered Respiratory Airflow

Low pass filter the respiratory airflow to remove cardiogenic airflow and other noise. The time constant is dynamically adjusted to be 1/40 of the current estimated length of the respiratory cycle $T_{TOT}$ (initialized to $STD\_T_{TOT}$ and updated below). This means that at high respiratory rates, there is only a short phase delay introduced by the filter, but at low respiratory rates, there is good rejection of cardiogenic airflow.

Mask On/Off Status

The mask is assumed to initially be off. An off-on transition is taken as occurring when the respiratory airflow first goes above 0.2 L/sec, and an on-off transition is taken as occurring if the mask pressure is less than 2 cmH$_2$O for more than 1.5 seconds.

Lead-in

Figure 6:
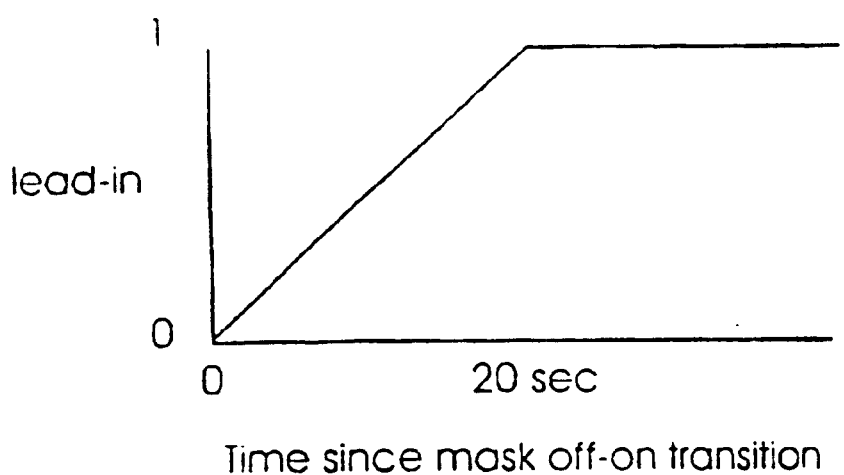
FIG. 6 shows calculation of a quantity "lead-in" as a function of time since the most recent mask off-on transition.

Lead-in is a quantity that runs from zero if the mask is off, or has just been donned, to 1.0 if the mask has been on for 20 seconds or more, as shown in FIG. 6.

Calculation of Instantaneous Jamming Index, J

J is the fuzzy extent to which the impedance of the leak has suddenly changed. It is calculated as the fuzzy extent to which the absolute magnitude of the respiratory airflow is large for longer than expected.

Figure 7:
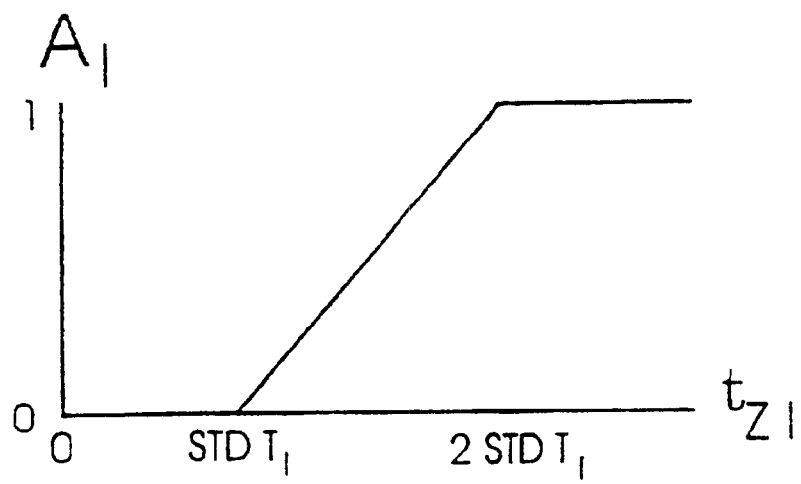
FIG. 7 shows a fuzzy membership function for fuzzy set $A_I$ as a function of time since the most recent expiratory-to-inspiratory (negative-to-positive) zero crossing of the respiratory airflow signal, such that the membership function measures the extent to which the respiratory airflow has been positive for longer than expected.

The fuzzy extent $A_I$ to which the airflow has been positive for longer than expected is calculated from the time $t_{ZI}$ since the last positive-going zero crossing of the calculated respiratory airflow signal, and the expected duration STD $T_I$ of a normal inspiration for the particular subject, using the fuzzy membership function shown in FIG. 7.

Figure 8:
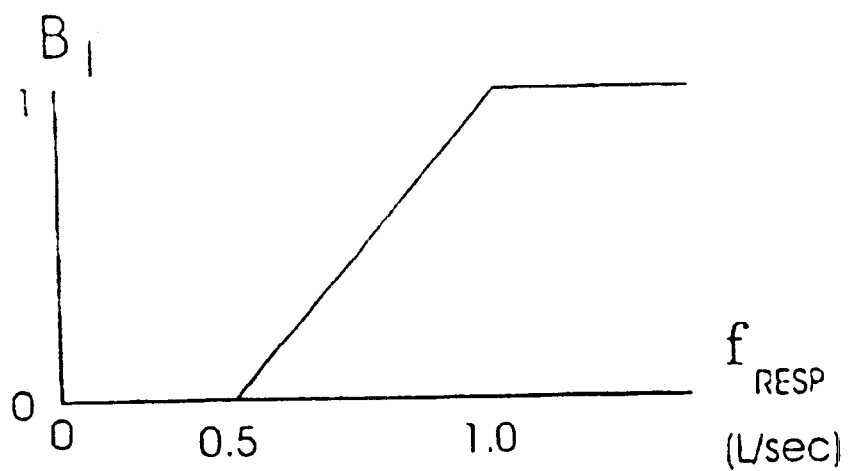
FIG. 8 shows a membership function for fuzzy set $B_I$ as a function of respiratory airflow, such that the membership function measures the extent to which respiratory airflow is large positive.

The fuzzy extent $B_I$ to which the airflow is large and positive is calculated from the instantaneous respiratory airflow using the fuzzy membership function shown in FIG. 8.

The fuzzy extent $I_I$ to which the leak has suddenly increased is calculated by calculating the fuzzy intersection (lesser) of $A_I$ and $B_I$.

Precisely symmetrical calculations are performed for expiration, deriving $I_E$ as the fuzzy extent to which the leak has suddenly decreased. $A_E$ is calculated from $T_{ZE}$ and $T_E$, $B_E$ is calculated from minus $f_{RESP}$, and $I_E$ is the fuzzy intersection of $A_E$ and $B_E$. The instantaneous jamming index J is calculated as the fuzzy union (larger) of indices $I_I$ and $I_E$.

Recent Peak Jamming

Figure 9:
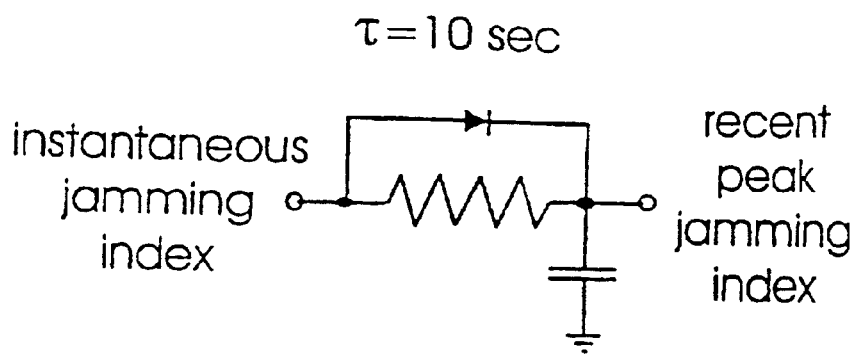
FIG. 9 shows an electrical analog of the calculation of a recent peak jamming index $J_{PEAK}$ from the instantaneous jamming index J.

If the instantaneous jamming index is larger than the current value of the recent peak jamming index, then the recent peak jamming index is set to equal the instantaneous jamming index. Otherwise, the recent peak jamming index is set to equal the instantaneous jamming index low pass filtered with a time constant of 10 seconds. An electrical analogy of the calculation is shown in FIG. 9.

Time Constant for Leak Conductance Calculations

If the conductance of the leak suddenly changes, then the calculated conductance will initially be incorrect, and will gradually approach the correct value at a rate which will be slow if the time constant of the low pass filters is long, and fast if the time constant is short. Conversely, if the impedance of the leak is steady, the longer the time constant the more accurate the calculation of the instantaneous leak. Therefore, it is desirable to lengthen the time constant to the extent that the leak is steady, reduce the time constant to the extent that the leak has suddenly changed, and to use intermediately longer or shorter time constants if it is intermediately the case that the leak is steady.

If there is a large and sudden increase in the conductance of the leak, then the calculated respiratory airflow will be incorrect. In particular, during apparent inspiration, the calculated respiratory airflow will be large positive for a time that is large compared with the expected duration of a normal inspiration. Conversely, if there is a sudden decrease in conductance of the leak, then during apparent expiration the calculated respiratory airflow will be large negative for a time that is large compared with the duration of normal expiration.

Figure 10:
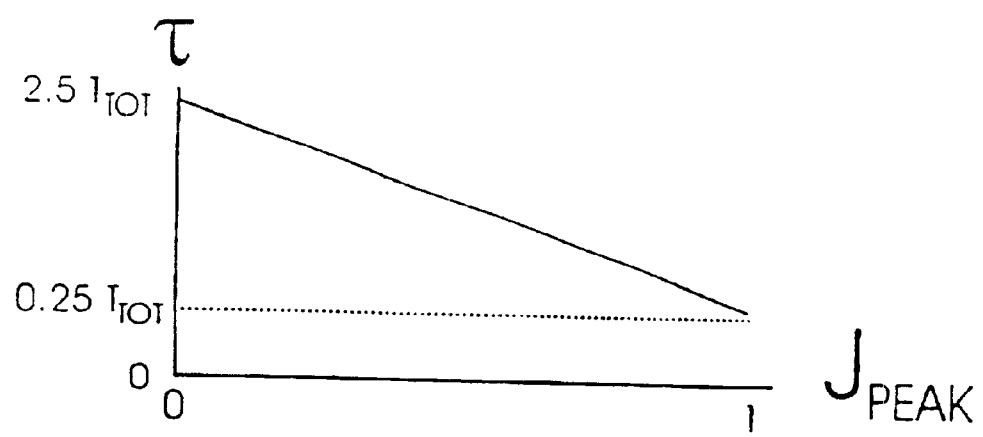
FIG. 10 shows the calculation of the time constant τ used in low pass filtering steps in the calculation of the conductance of a leak, as a function of the recent peak jamming index $J_{PEAK}$.

Therefore, the time constant for the calculation of the conductance of the leak is adjusted depending on $J_{PEAK}$, which is a measure of the fuzzy extent that the leak has recently suddenly changed, as shown in FIG. 10.

In operation, to the extent that there has recently been a sudden and large change in the leak, $J_{PEAK}$ will be large, and the time constant for the calculation of the conductance of the leak will be small, allowing rapid convergence on the new value of the leakage conductance. Conversely, if the leak is steady for a long time, $J_{PEAK}$ will be small, and the time constant for calculation of the leakage conductance will be large, enabling accurate calculation of the instantaneous respiratory airflow. In the spectrum of intermediate situations, where the calculated instantaneous respiratory airflow is larger and for longer periods, $J_{PEAK}$ will be progressively larger, and the time constant for the calculation of the leak will progressively reduce. For example, at a moment in time where it is uncertain whether the leak is in fact constant, and the subject has merely commenced a large sigh, or whether in fact there has been a sudden increase in the leak, the index will be of an intermediate value, and the time constant for calculation of the impedance of the leak will also be of an intermediate value. The advantage is that some corrective action will occur very early, but without momentary total loss of knowledge of the impedance of the leak.

Instantaneous Phase in Respiratory Cycle

Figure 11:
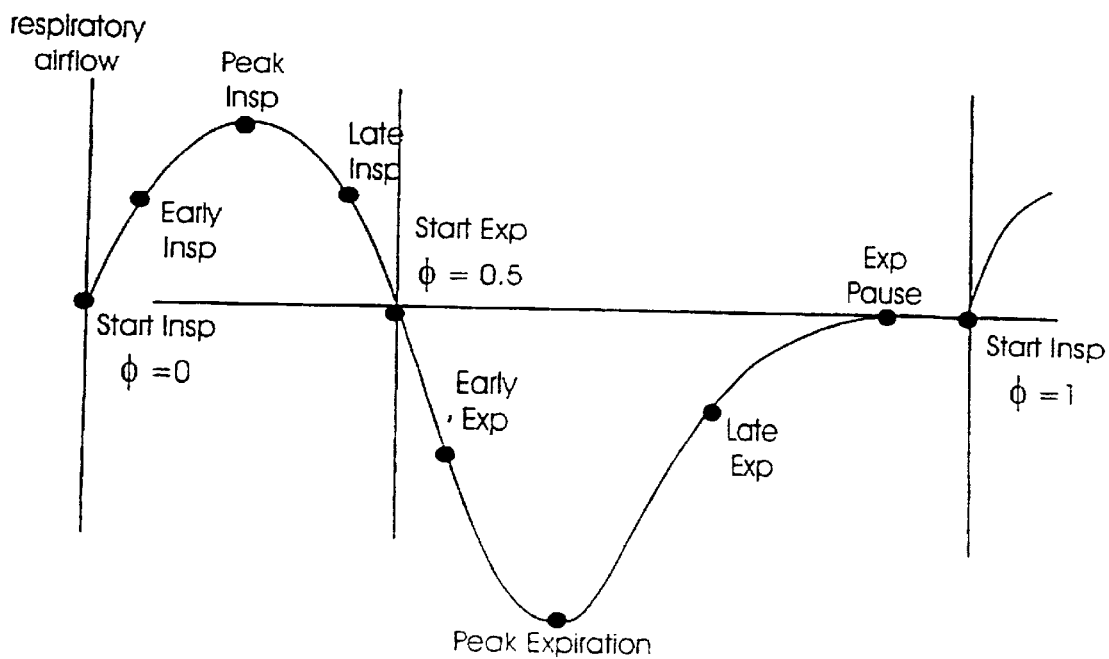
FIG. 11 shows a prototypical respiratory flow-time curve, with time an the x-axis, marking nine features.

The current phase $\phi$ runs from 0 for start of inspiration to 0.5 for start of expiration to 1.0 for end expiration=start of next inspiration. Nine separate features (peaks, zero crossings, plateaux, and some intermediate points) are identified on the waveform, as shown in FIG. 11.

Calculation of Normalized Respiratory Airflow

Figure 12:
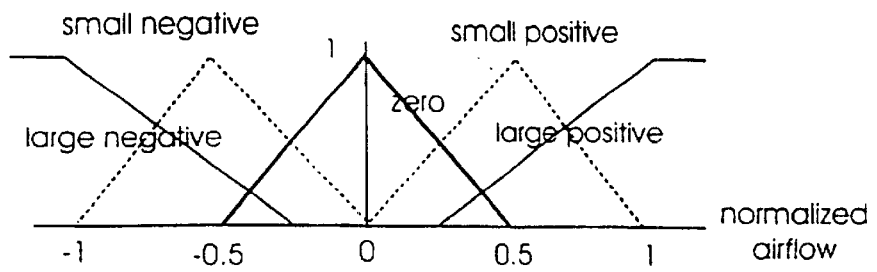
FIG. 12 shows membership functions for fuzzy sets "large negative", "small negative", "zero" "small positive", and "large positive" as functions of normalized respiratory airflow according to a second embodiment of the invention.

The filtered respiratory airflow is normalized with respect to the user specified target ventilation as follows:

standard airflow=target ventilation/7.5 L/min $f'$=filtered respiratory airflow/standard airflow Next, the fuzzy membership in fuzzy sets large negative, small negative, zero, small positive, and large positive, describing the instantaneous airflow is calculated using the membership functions shown in FIG. 12. For example, if the normalized airflow is 0.25, then the airflow is large negative to extent 0.0, small negative to extent 0.0, zero to extent 0.5, small positive to extent 0.5, large positive to extent 0.00.

Calculation of Normalized Rate of Change of Airflow

Figure 13:
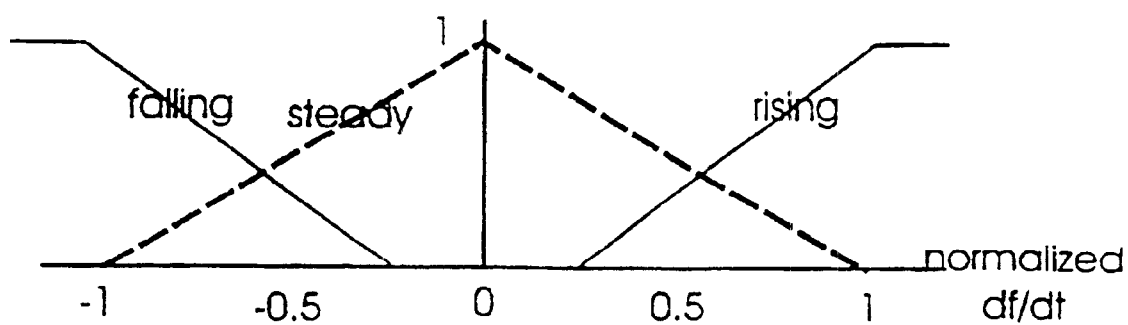
FIG. 13 shows membership functions for fuzzy sets "falling", "steady", and "rising" as functions of normalized rate of change of respiratory airflow df/dt according to a second embodiment of the invention.

The rate of change of filtered respiratory airflow is calculated and normalized to a target ventilation of 7.5 L/min at 15 breaths/min as follows:

standard df/dt=standard airflow*target frequency/15 calculate d(filtered airflow)/dt low pass filter with a time constant of 8/50 seconds normalize by dividing by standard df/dt Now evaluate the membership of normalized df/dt in the fuzzy sets falling, steady, and rising, whose membership function are shown in FIG. 13.

Figure 14:
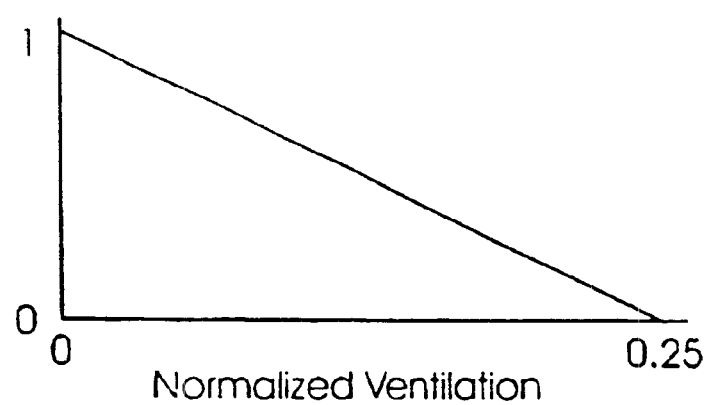
FIG. 14 shows the membership function for fuzzy set "hypopnea"

Calculation of Ventilation, Normalized Ventilation, and Hypopnea ventilation=abs(respiratory airflow), low pass filtered with a time constant of STD $T_{TOT}$, normalized ventilation=ventilation/standard airflow Hypopnea is the fuzzy extent to which the normalized ventilation is zero. The membership function for hypopnea is shown in FIG. 14.

Calculation of Recent Ventilation, Normalized Recent Ventilation, and Hyperpnea

Figure 15:
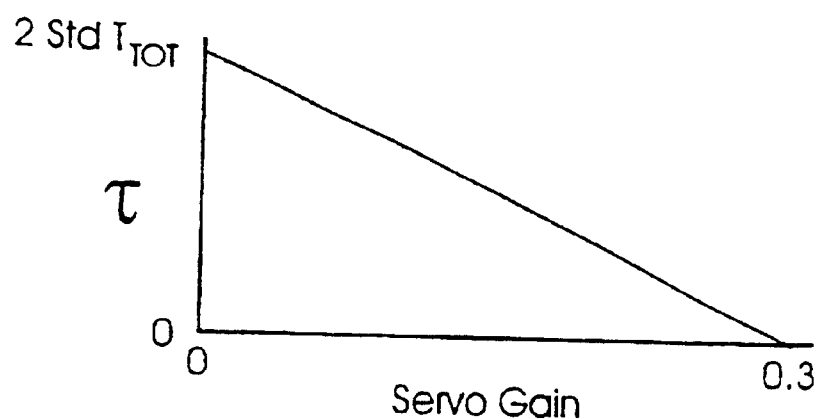
FIG. 15 shows the calculation of the time constant τ for calculation of normalized recent ventilation, as a function of "servo gain" being the gain used for servo-control of minute ventilation to at least exceed a specified target ventilation; of normalized recent ventilation.

Recent ventilation is also a low pass filtered abs (respiratory airflow), but filtered with an adjustable time constant, calculated from servo gain (specified by the user) as shown in FIG. 15. For example, if the servo gain is set to the maximum value of 0.3, the time constant is zero, and recent ventilation equals instantaneous abs(respiratory airflow). Conversely, if servo gain is zero, the time constant is twice STD $T_{TOT}$, the expected length of a typical breath.

Figure 16:
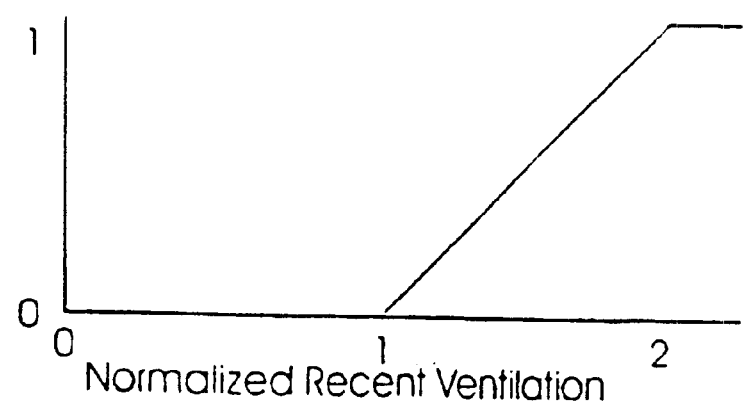
FIG. 16 shows the membership function for fuzzy set "hypernea" as a function of normalized recent ventilation.

Target absolute airflow=2*target ventilation normalized recent ventilation=recent ventilation/target absolute airflow Hyperpnea is the fuzzy extent to which the recent ventilation is large. The membership function for hyperpnea is shown in FIG. 16.

Big Leak

Figure 17:
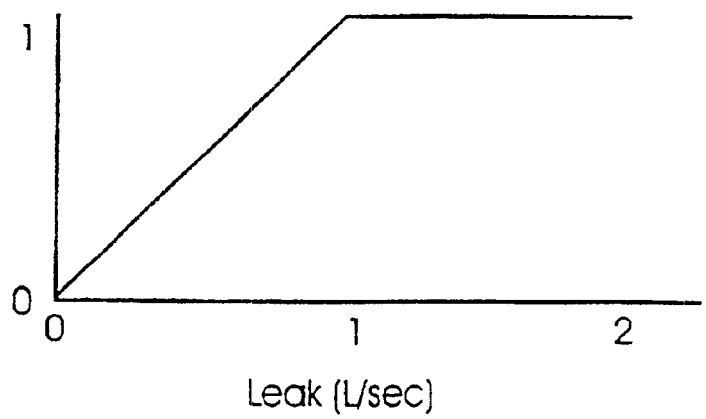
FIG. 17 shows the membership function for fuzzy set "big leak" as a function of leak.

The fuzzy extent to which there is a big leak is calculated from the membership function shown in FIG. 17.

Additional fuzzy sets concerned with fuzzy "triggering"

Figure 18:
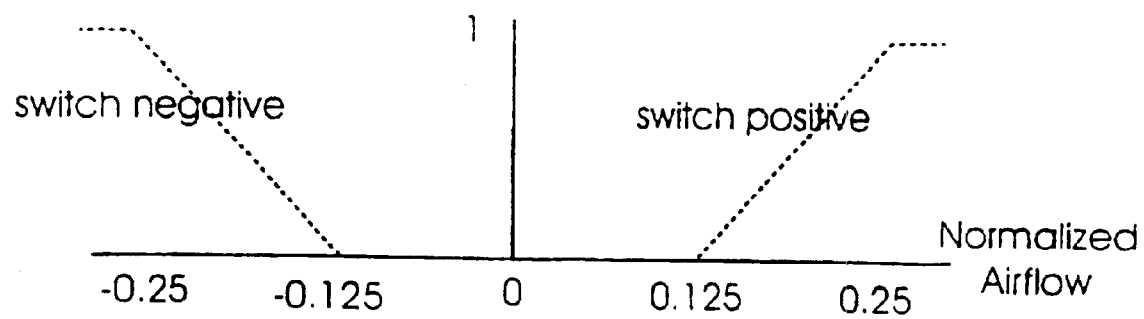
FIG. 18 shows the membership functions for fuzzy sets "switch negative" and "switch positive" as a function of normalized respiratory airflow.
Figure 19:
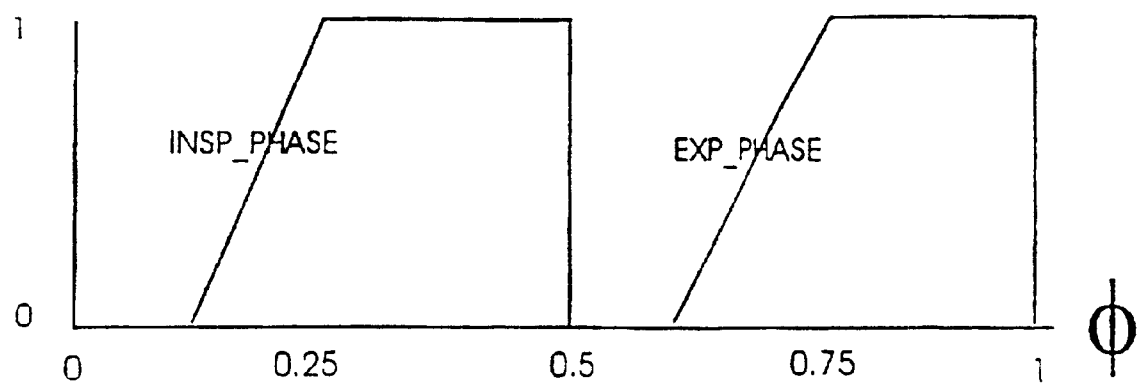
FIG. 19 shows the membership functions for fuzzy sets "insp_phase" and "exp_phase" as functions of the instantaneous phase in the respiratory cycle $\phi$.

Membership in fuzzy sets switch negative and switch positive are calculated from the normalized respiratory airflow using the membership functions shown in FIG. 18, and membership in fuzzy sets insp_phase are calculated from the current phase f using the membership functions shown in FIG. 19.

Fuzzy Inference Rules for Phase

Figure 20:
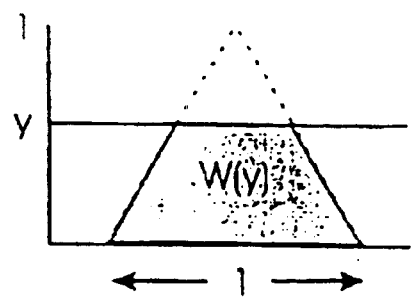
FIG. 20 shows schematically how function W(y), used in defuzzification, calculates the area (shaded) of an isosceles triangle of unit base and height cut off below height y.

Procedure W(y) calculates the area of an isosceles triangle of unit height and unit base, truncated at height y as shown in FIG. 20. In the calculations that follow, recall that fuzzy intersection a AND b is the smaller of a and b, fuzzy union a OR b is the larger of a and b, and fuzzy negation NOT a is 1-a.

The first fuzzy rule indicates that lacking any other information the phase is to increase at a standard rate. This rule is unconditionally true, and has a very heavy weighting, especially if there is a large leak, or there has recently been a sudden change in the leak, or there is a hypopnea.

$W_{STANDARD}$=8+16*$J_{PEAK}$+16*hyopopnea+16*big leak

The next batch of fuzzy rules correspond to the detection of various features of a typical flow-vs-time curve. These rules all have unit weighting, and are conditional upon the fuzzy membership in the indicated sets:

$W_{EARLY\ INSP}$=W(rise and small positive)

$W_{PEAK\ INSP}$=W(large positive AND steady AND NOT recent peak jamming)

$W_{LATE\ INSP}$=W(fall AND small positive)

$W_{EARLY\ EXP}$=W(fall AND small negative)

$W_{PEAK\ EXP}$=W(large negative AND steady)

$W_{LATE\ EXP}$=W(rise AND small negative)

The next rule indicates that there is a legitimate expiratory pause (as opposed to an apnea) if there has been a recent hyperpnea and the leak has not recently changed:

$W_{PAUSE}$=(hyperpnea AND NOT $J_{PEAK}$)*W(steady AND zero)

Recalling that the time constant for hyperpnea gets shorter as servo gain increases, the permitted length of expiratory pause gets shorter and shorter as the servo gain increases, and becomes zero at maximum servo gain. The rationale for this is that (i) high servo gain plus long pauses in breathing will result in "hunting" of the servo-controller, and (ii) in general high servo gain is used if the subject's chemoreceptor responses are very brisk, and suppression of long apneas or hypopneas will help prevent the subject's own internal servo-control from hunting, thereby helping prevent Cheyne-Stokes breathing.

Finally, there are two phase-switching rules. During regular quiet breathing at roughly the expected rate, these rules should not strongly activate, but they are there to handle irregular breathing or breathing at unusual rates. They have very heavy weightings.

$W_{TRIG\ INSP}$=32 W(expiratory phase AND switch positive)

$W_{TRIG\ EXP}$=32 W(inspiratory phase AND switch negative)

Defuzzification

For each of the ten fuzzy rules above, we attach phase angles fN, as shown in Table ZZZ. Note that φN are in revolutions, not radians. We now place the ten masses W(N) calculated above at the appropriate phase angles $\phi_N$ around the unit circle, and take the centroid.

| Rule | N | $\phi_N$ |
|---|---|---|
| STANDARD | 1 | current φ |
| TRIG INSP | 2 | 0.00 |
| EARLY INSP | 3 | 0.10 |
| PEAK INSP | 4 | 0.30 |
| LATE INSP | 5 | 0.50 |
| TRIG EXP | 6 | 0.5 + 0.05 k |
| EARLY EXP | 7 | 0.5 + 0.10 k |
| PEAK EXP | 8 | 0.5 + 0.20 k |
| LATE EXP | 9 | 0.5 + 0.4 k |
| EXP PAUSE | 10 | 0.51 + 0.5 k | where k=STD $T_I$/STD $T_E$.

Note that if the user has entered very short duty cycle, k will be small. For example a normal duty cycle is 40%, giving k=40/60=0.67. Thus the expiratory peak will be associated with a phase angle of 0.5+0.2*0.67=0.63, corresponding 26% of the way into expiratory time, and the expiratory pause would start at 0.5+0.5*0.67=0.83, corresponding to 67% of the way into expiratory time. Conversely, if the duty cycle is set to 20% in a patient with severe obstructive lung disease, features 6 through 10 will be skewed or compressed into early expiration, generating an appropriately longer expiratory pause.

The new estimate of the phase is the centroid, in polar coordinates, of the above ten rules:

$$\text{centroid} = \arctan\left(\frac{\sum W_N \sin\phi_N}{\sum W_N \cos\phi_N}\right)$$

The change in phase dφ from the current phase φ to the centroid is calculated in polar coordinates. Thus is the centroid is 0.01 and the current phase is 0.99, the change in phase is dφ=0.02. Conversely, if the centroid is 0.99 and the current phase is 0.01, then dφ=−0.02. The new phase is then set to the centroid:

φ=centroid

This concludes the calculation of the instantaneous phase in the respiratory cycle φ.

Estimated mean duration of inspiration, expiration, cycle time, and respiratory rate If the current phase is inspiratory (φ<0.5) the estimated duration of inspiration $T_I$ is updated:

LP(dφ$_I$)=low pass filtered dφ with a time constant of 4*STD $T_{TOT}$

Clip LP(dφ$_I$) to the range (0.5/STD $T_I$)/2 to 4(0.5/STD $T_I$)

$T_I$=0.5/clipped LP (dφI)

Conversely, if the current phase is expiratory, (φ>=0.5) the estimated duration of expiration $T_E$ is updated:

LP(dφ$_E$)=low pass filtered dφ with a time constant of 4*STD $T_{TOT}$

Clip LP(dφE) to the range (0.5/STD $T_E$)/2 to 4(0.5/STD $T_E$)

$T_E$=0.5/clipped LP(dφ$_E$)

The purpose of the clipping is firstly to prevent division by zero, and also so that the calculated $T_I$ and $T_E$ are never more than a factor of 4 shorter of a factor of 2 longer than expected.

Finally, the observed mean duration of a breath $T_{TOT}$ and respiratory rate RR are:

$T_{TOT}$=$T_I$+$T_E$

RR=60/$T_{TOT}$

Resistive unloading

The resistive unloading is the pressure drop across the patient's upper and lower airways, calculated from the respiratory airflow and resistance value stored in SRAM f=respiratory airflow truncated to +/−2 L/sec resistive unloading=airway resistance *f+ upper airway resistance*$f^2$*sign(f)

Instantaneous Elastic Assistance

The purpose of the instantaneous elastic assistance is to provide a pressure which balances some or all of the elastic deflating pressure supplied by the springiness of the lungs and chest wall (instantaneous elastic pressure), plus an additional component required to servo-control the minute ventilation to at least exceed on average a pre-set target ventilation. In addition, a minimum swing, always present, is added to the total. The user-specified parameter elastance is preset to say 50–75% of the known or estimated elastance of the patient's lung and chest wall. The various components are calculated as follows:

Instantaneous assistance based on minimum pressure swing set by physician:

instantaneous minimum assistance=minimum swing * Π(φ)

Elastic assistance required to servo-control ventilation to equal or exceed target The quantity servo swing is the additional pressure modulation amplitude required to servo-control the minute ventilation to at least equal on average a pre-set target ventilation.

Minute ventilation is defined as the total number of litres inspired or expired per minute. However, we can't wait for a whole minute, or even several seconds, to calculate it, because we wish to be able to prevent apneas or hypopneas lasting even a few seconds, and a PI controller based on an average ventilation over a few seconds would be either sluggish or unstable.

The quantity actually servo-controlled is half the absolute value of the instantaneous respiratory airflow. A simple clipped integral controller with no damping works very satisfactorily. The controller gain and maximum output ramp up over the first few seconds after putting the mask on.

If we have had a sudden increase in mouth leak, airflow will be nonzero for a long time. A side effect is that the ventilation will be falsely measured as well above target, and the amount of servo assistance will be falsely reduced to zero. To prevent this, to the extent that the fuzzy recent peak jamming index is large, we hold the degree of servo assistance at its recent average value, prior to the jamming.

The algorithm for calculating servo swing is as follows:

error=target ventilation−abs(respiratory airflow)/2 servo swing=S error*servo gain*sample interval clip servo swing to range 0 to 20 cmH$_2$O*lead-in set recent servo swing=servo swing low pass filtered with a time constant of 25sec.

clip servo swing to be at most J$_{PEAK}$*recent servo swing

The instantaneous servo assistance is calculatged by multiplying servo swing by the previously calculatged pressure waveform template;

instantaneous servo assistance=servo swing*II($\phi$)

Estimating Instantaneous Elastic Pressure

The instantaneous pressure required to unload the elastic work of inspiring against the user-specified elastance is the specified elastance time the instantaneous inspired volume. Unfortunately, calculating instantaneous inspired volume simply by integrating respiratory airflow with respect to time does not work in practice for three reasons: first by leaks cause explosive run-away of the integration. Secondly, the integrator is reset at the start of each inspiration, and this point is difficult to detect reliably. Thirdly, and crucially, if the patient is making no effort, nothing wil happen.

Therefore, four separate estimates are made, and a weighted average taken.

Estimate 1: Exact instantaneous elastic recoil calculated from instantaneous tidal volume, with a correction for sudden change in leak The first estimate is the instantaneous elastic recoil of a specified elastance at the estimated instantaneous inspired volume, calculated by multiplying the specified elastance by the integral of a weighted respiratory airflow with respect to time, reset to zero if the respiratory phase is expiratory. The respiratory airflow is weighted by the fuzzy negation of the recent peak jamming index J$_{PEAK}$, to partly ameliorate an explosive run-away of the integral during brief periods of sudden increase in leak, before the leak detector has had time to adapt to the changing leak. In the case where the leak is very steady, J$_{PEAK}$ will be zero, the weighting will be unity, and the inspired volume will be calculated normally and correctly. In the case where the leak increases suddenly, J$_{PEAK}$ will rapidly increase, the weighting will decrease, and although typically the calculated inspired volume will be incorrect, the over-estimation of inspired volume will be ameliorated. Calculations are as follows:

Instantaneous volume=integral of respiratory airflow⁻(I−J$_{PEAK}$) dt if phase is expiratory (0.5<$\phi$<1.0 revolutions) reset integral to zero estimate 1=instantaneous volume*elastance Estimate 2: based on assumption that the tidal volume equals the target tidal volume The quantity standard swing is the additional pressure modulation amplitude that would unload the specified elastance for a breath of a preset target tidal volume.

target tidal volume=target ventilation/target frequency standard swing=elastance*target tidal volume estimate 2=standard swing*II($\phi$)

Estimate 3: based on assumption that the tidal volume equals the target tidal volume divided by the observed mean respiratory rate RR calculated previously.

Estimate 3=elastance*target ventilation/RR*II($\phi$)

Estimate 4: based on assumption that this breath is much like recent breaths

The instantaneous assistance based on the assumption that the elastic work for this breath is similar to that for recent breaths is calculated as follows:

LP elastic assistance=instantaneous elastic assistance low pass filtered with a time constant of 2 STD T$_{TOT}$ estimate 4=LP elastic assistance*II($\phi$)/P$_{BAR}$ The above algorithm works correctly even if II($\phi$) is dynamically changed on-the-fly by the user, from square to a smooth or vice versa. For example, if an 8 cmH2O square wave (II$_{BAR}$=1) adequately assists the patient, then a sawtooth wave (II$_{BAR}$=0.5) will require 16 cmH$_2$O swing to produce the same average assistance.

Best Estimate of Instantaneous Elastic Recoil Pressure

Next, calculate the pressure required to unload a best estimate of the actual elastic recoil pressure based on a weighted average of the above. If II($\phi$) is set to the smoothest setting, the estimate is based equally on all the above estimates of instantaneous elastic recoil. If II($\phi$) is a square wave, the estimate is based on all the above estimates except for estimate 1, because a square wave is maximal at $\phi$=0, whereas estimate 1 is zero at $\phi$=0. Intermediate waveforms are handled intermediately. Quantity smoothness runs from zero for a square wave to 1 for a waveform time constant of 0.3 or above.

smoothness=waveform time constant/0.3 instantaneous recoil=(smoothness*estimate 1+estimate 2+estimate 3+estimate 4)/(smoothness+3)

Now add the estimates based on minimum and servo swing, truncate so as not to exceed a maximum swing set by the user. Reduce (lead in gradually) if the mask has only just been put on.

I=instantaneous minimum assistance+instantaneous servo assistance+instantaneous recoil Truncate I to be less than preset maximum permissible swing instantaneous elastic assistance=I*lead-in This completes the calculation of instantaneous elastic assistance.

Desired Pressure at Sensor desired sensor pressure=epap+hose pressure loss+resistive unloading+instantaneous elastic assistance Servo Control of Motor Speed In the final step, the measured pressure at the sensor is servo-controlled to equal the desired sensor pressure, using for example a clipped pseudodifferential controller to adjust the motor current. Reference can be made to FIG. 1 in this regard.

Device Performance

FIGS. 21–27 each show an actual 60 second recording displaying an aspect of the second embodiment. All recordings are from a normal subject trained to perform the required manoeuvres. Calculated respiratory airflow, mask pressure, and respiratory phase are calculated using the algorithms disclosed above, output via a serial port, and plotted digitally.

In FIGS. 21–26 respiratory airflow is shown as the darker tracing, the vertical scale for flow being ±L/sec, inspiration upwards. The vertical scale for the pressure (light trace) is 0.2 $cmH_2O$.

Figure 21:
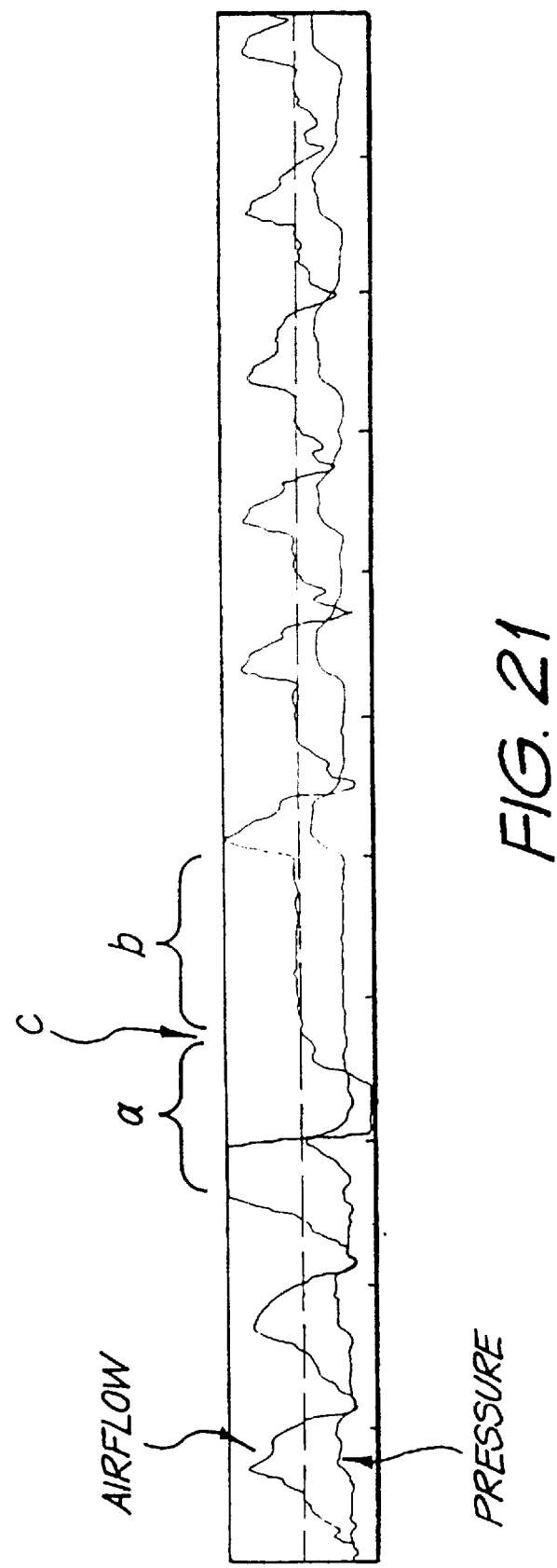
FIGS. 21–26 show actual 60 second flow and pressure tracings from the second embodiment of the invention during operation; the vertical scale for flow (heavy trace) is ±1 L/sec, inspiration upwards and the vertical scale for the pressure (light trace) is 0–25 cm $H_2O$; where.
Figure 22:
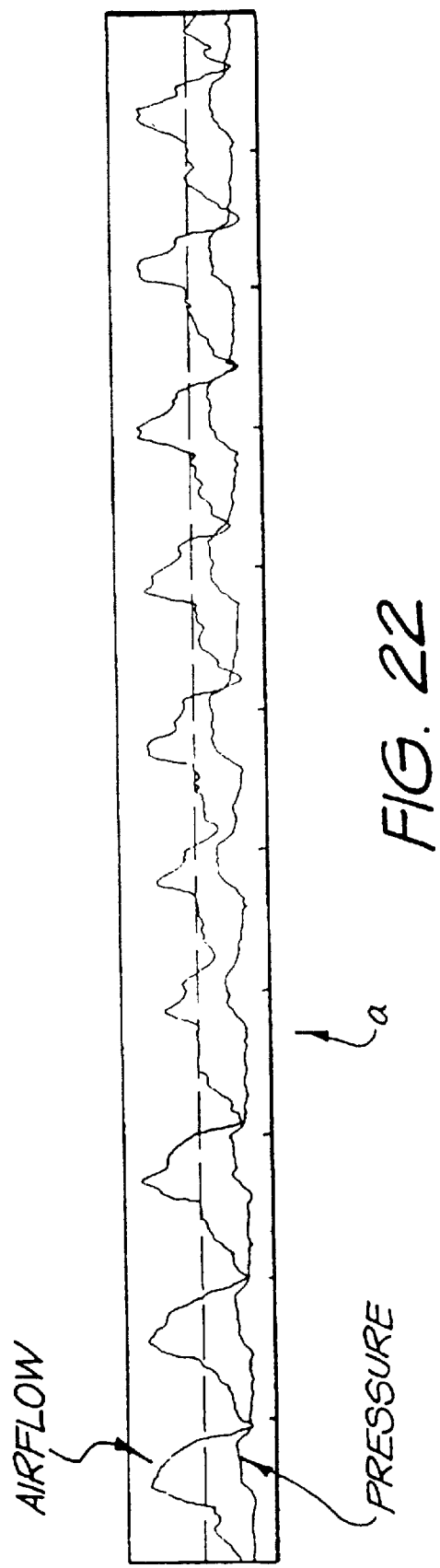
Figure 23:
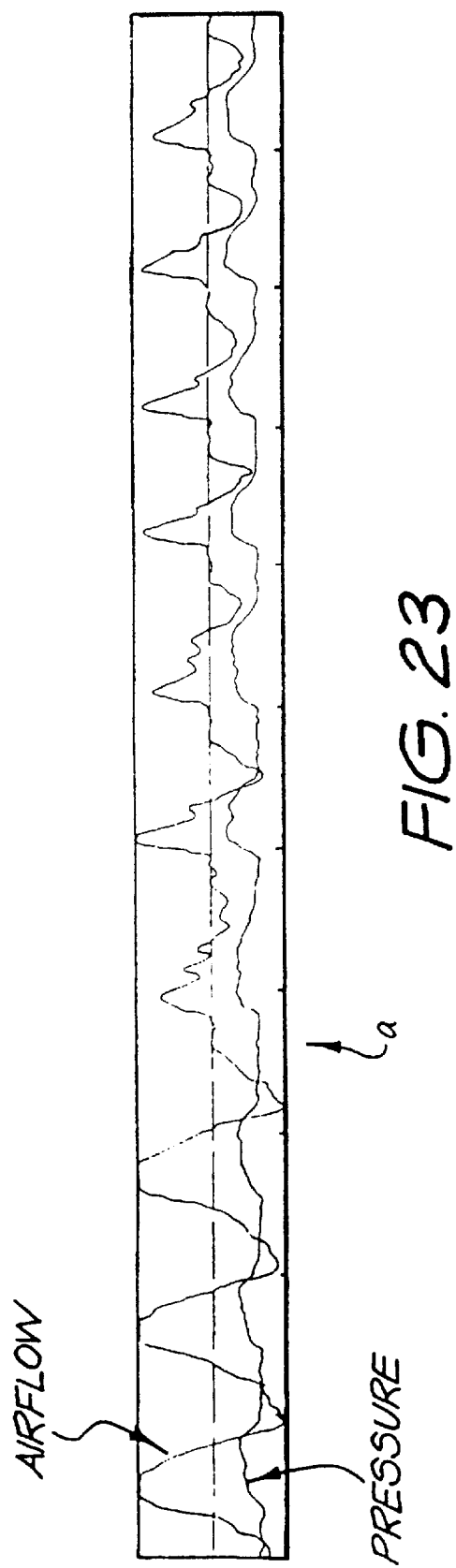

FIG. 21 is recorded with the servo gain set to 0.1 $cmH_2O$/L/sec/sec, which is suitable for subjects with normal chemoflexes. The subject is breathing well above the minimum ventilation, and a particularly deep breath (sigh) is taken at point (a). As is usual, respiratory effort ceases following the sigh, at point (c). The device correctly permits a short central apnea (b), as indicated by the device remaining at the end expiratory pressure during the period marked (b). Conversely FIG. 22 shows that if there is no preceding deep breath, when efforts cease at (a), the pressure correctly continues to cycle, thus preventing any hypoxia FIG. 23 is recorded with servo gain set high, as would be appropriate for a subject with abnormally high chemoreflexes such as is typically the case with Cheyne-Stokes breathing. Now when effort ceases at arrow (a), pressure continues to cycle and a central apnea is no longer permitted, despite preceding deep breathing. This is advantageous for preventing the next cycle of Cheyne-Stokes breathing.

The above correct behaviour is also exhibited by a time mode device, but is very different to that of a spontaneous mode bilevel device, or equally of proportional assist ventilation, both of which would fail to cycle after all central apneas, regardless of appropriateness.

Figure 24:
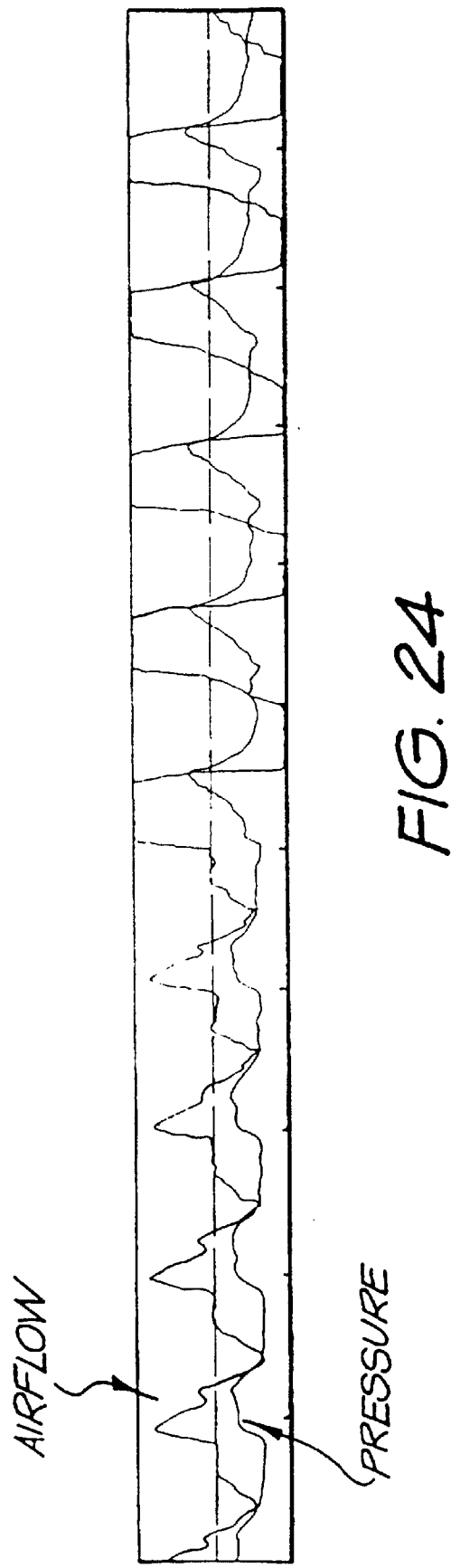

FIG. 24 shows automatically increasing end-inspiratory pressure as the subject makes voluntarily deeper inspiratory efforts. The desirable behaviour is in common with PAV, but is different to that of a simple bilevel device, which would maintain a constant level of support despite an increased patient requirement, or to a volume cycled device, which would actually decrease support at a time of increasing need.

Figure 25:
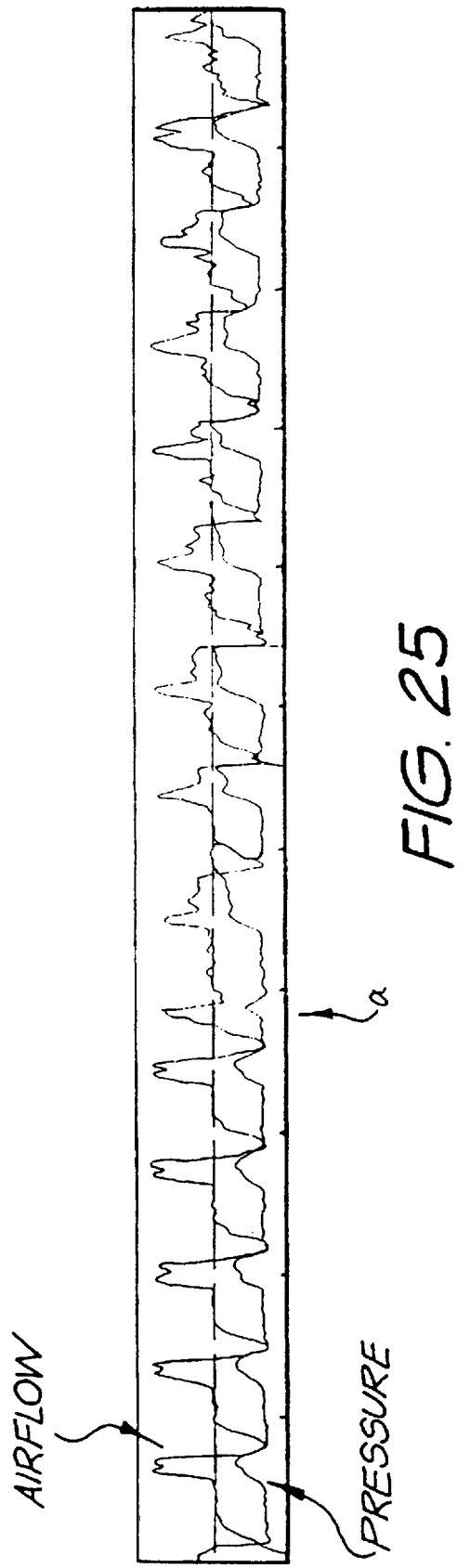

FIG. 25 is recorded with a somewhat more square waveform selected. This figure shows automatically increasing pressure support when the subject voluntarily attempts to resist by stiffening the chest wall at point (a). This desirable behaviour is common with PAV and volume cycled devices, with the expectation that PAV cannot selectively deliver a squarer waveform. It is distinct from a simple bilevel device which would not augment the level of support with increasing need.

Figure 26:
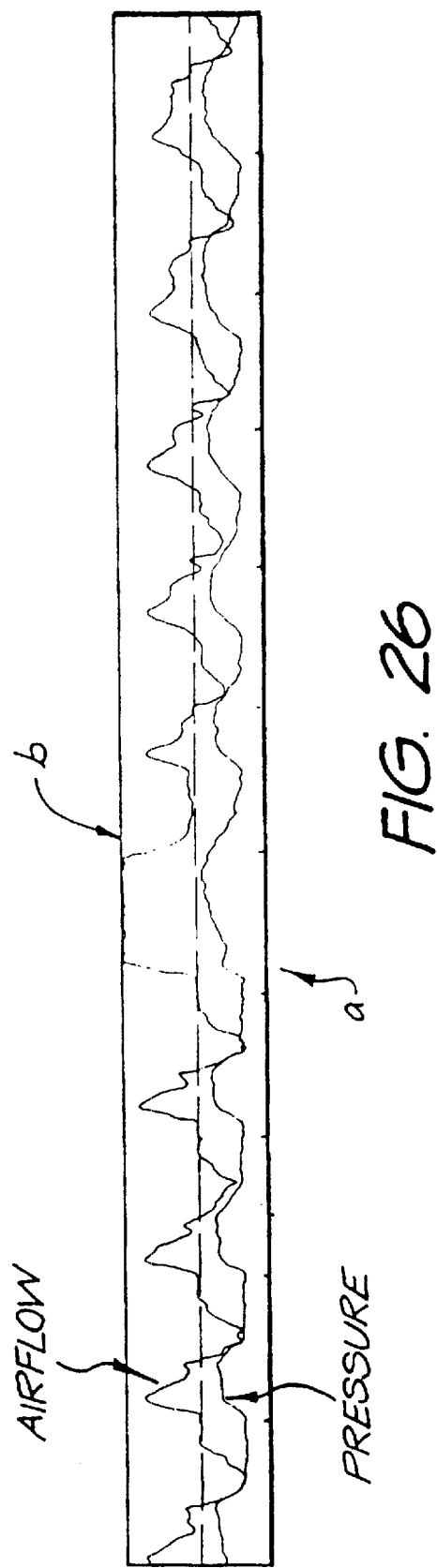
Figure 27:
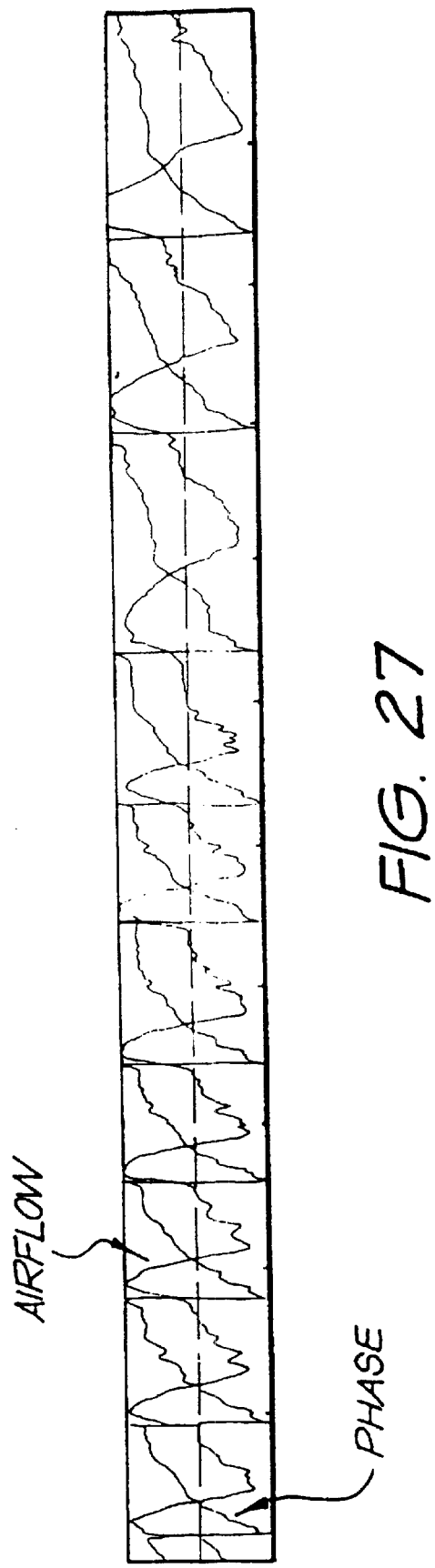
FIG. 27 shows an actual 60 second tracing showing respiratory airflow (heavy trace, ±1 L/sec full scale) and instantaneous phase (light trace, 0–1 revolution full scale).

FIG. 26 shows that with sudden onset of a severe 1.4 L/sec leak at (a), the flow signal returns to baseline (b) within the span of a single breath, and pressure continues to cycle correctly throughout. Although timed mode devices can also continue to cycle correctly in the face of sudden changing leak, the are unable to follow the subject's respiratory rate when required (as shown in FIG. 27). Other known bilevel devices and PAV mis-trigger for longer or shorter periods following onset of a sudden sever leak, and PAV can delivery greatly excessive pressures under these conditions.

FIG. 27 shows an actual 60 second tracing showing respiratory airflow (heavy trace ±1 L/sec full scale) and respiratory phase as a continuous variable (light trace, 0 to 1 revolution), with high respiratory rate in the left half of the trace and low respiratory rate in the right half of the trace. This trace demonstrates that the invention can determine phase as a continuous variable.

Advantageous Aspects of Embodiments of the Invention

Use of phase as a continuous variable

In the prior art, phase is taken as a categorical variable, with two values: inspiration and expiration. Errors in the detection of start of inspiration and start of expiration produce categorical errors in delivered pressure. Conversely, here, phase is treated as a continuous variable having values between zero and unity. Thus categorical errors in measurement of phase are avoided.

Adjustable filter frequency and allowance for phase delay

By using a short time constant when the subject is breathing rapidly, and a long time constant when the subject is breathing slowly, the filter introduces a fixed phase delay which is always a small fraction of a respiratory cycle. Thus unnecessary phase delays can be avoided, but cardiogenic artifact can be rejected in subjects who are breathing slowly. Furthermore, because phase is treated as a continuous variable, it is possible to largely compensate for the delay in the low pass filter.

Within-breath pressure regulation as a continuous function of respiratory phase

With all prior art there is an intrusive discontinuous change in pressure, either at the start of inspiration or at the start of expiration. Here, the pressure change is continuous, and therefore more comfortable.

With proportional assist ventilation, the instantaneous pressure is a function of instantaneous volume into the breath. This means that a sudden large leak can cause explosive pressure run-away. Here, where instantaneous pressure is a function of instantaneous phase rather than tidal volume, this is avoided.

Between-breath pressure-regulation as a function of average inspiratory duration Average inspiratory duration is easier to calculate in the presence of leak than is tidal volume. By taking advantage of a correlation between average inspiratory duration and average tidal volume, it is possible to adjust the amplitude of modulation to suit the average tidal volume.

Provision of a pressure component for unloading turbulent upper airway resistance, and avoiding cardiogenic pressure instabilities Although Younes describes the use of a component of pressure proportional to the square of respiratory airflow to unload the resistance of external apparatus, the resistance of the external apparatus in embodiments of the present invention is typically negligible. Conversely, embodiments of the present invention describes two uses for such a component proportional to the square of respiratory airflow that were not anticipated by Younes. Firstly, sleeping subjects, and subjects with a blocked nose, have a large resistance proportional to the square of airflow, and a pressure component proportional to the square of airflow can be used to unload the anatomical upper airway resistance. Secondly, small nonrespiratory airflow components due to heartbeat or other artifact, when squared, produces negligible pressure modulation, so that the use of such a component yields relative immunity to such nonrespiratory airflow.

Smooth transition between spontaneous and controlled breathing

There is a smooth, seamless gradation from flexibly tracking the subject's respiratory pattern during spontaneous breathing well above the target ventilation, to fully controlling the duration, depth, and phase of breathing if the subject is making no efforts, via a transitional period in which the subject can make progressively smaller changes to the timing and depth of breathing. A smooth transition avoids categorization errors when ventilation is near but not at the desired threshold. The advantage is that the transition from spontaneous to controlled ventilation occurs unobtrusively to the subject. This can be especially important in a subject attempting to go to sleep. A similar smooth transition can occur in the reverse direction, as a subject awakens and resumes spontaneous respiratory efforts.

What is claimed is:

1. A method for providing ventilatory assistance in a spontaneously breathing subject, comprising the steps, performed at repeated sampling intervals, of:
    calculating the instantaneous phase $\phi$ in the respiratory cycle as a continuous variable from 0 to 1 revolution,
    selecting a desired pressure modulation amplitude A,
    calculating a desired instantaneous delivery pressure as a function of an end expiratory pressure plus the desired pressure modulation amplitude A multiplied by the value of a waveform template function $\Pi(\phi)$ at the calculated instantaneous phase $\phi$, and
    delivering pressure to said subject at the calculated desired instantaneous delivery pressure.

2. A method as in claim 1, wherein the selected desired pressure modulation amplitude A includes a fixed amplitude.

3. A method as in claim 1, wherein the selected desired pressure modulation amplitude A includes a component equal to the elastance multiplied by an estimate of the subject's tidal volume.

4. A method as in claim 1, wherein the selected desired pressure modulation amplitude A includes a component calculated using the sub-steps of:
    specifying an expected breath duration,
    specifying a present pressure modulation amplitude to apply for said expected breath duration,
    calculating the actual breath duration of said subject, and
    calculating the component of said pressure modulation amplitude as a function of at least said specified preset pressure modulation amplitude multiplied by said calculated actual breath duration divided by the specified expected breath duration.

5. A method as in claim 1 wherein the phase in the respiratory cycle is calculated using the sub-steps of:
    determining the extent to which the subject is adequately ventilated,
    to said extent setting the phase in the respiratory cycle in accordance with the subject's respiratory airflow, and
    to the converse extent setting the phase in accordance with a preset respiratory rate.

6. A method as in claim 1, wherein the phase in the respiratory cycle is calculated using the sub-steps of:
    estimating respiratory airflow,
    deriving a measure of mask leak stability,
    to the extent that mask leak is stable, calculating the phase in accordance with the estimate of respiratory airflow, and
    to the converse extent, calculating the phase in the respiratory cycle in accordance with a preset respiratory rate.

7. A method as in claim 1, wherein the selected desired pressure modulation amplitude includes a component chosen to servo-control the degree of ventilation to at least exceed a specified ventilation.

8. A method as in claim 7, wherein said component is calculated using the sub-steps of:
    calculating an error term proportional to the absolute value of estimated respiratory airflow minus twice said specified ventilation, and
    setting said component proportional to the time integral of said error term.

9. A method as in claim 8, wherein the time integral is clipped to fall between a preset minimum and a preset maximum.

10. An apparatus for providing ventilatory assistance in a spontaneously breathing subject comprising:
    a delivery means for supplying breathable gas at a controllable pressure to a subject,
    a sealed connection means between said delivery means and a subject's airway,
    a means for determining an airflow signal from said connection means, and
    a controller with programmed instructions for controlling:
        (a) a calculation of an instantaneous phase $\phi$ in a respiratory cycle as a continuous variable from 0 to 1 revolution from data representing said airflow signal;
        (b) a selection of a desired pressure modulation amplitude A;
        (c) a calculation of a desired instantaneous delivery pressure as a function of an end expiratory pressure plus the desired pressure modulation amplitude A multiplied by the value of a waveform template function $\Pi(\phi)$ at the calculated instantaneous phase $\phi$; and
        (d) a delivery of pressure to said subject at the calculated desired instantaneous delivery pressure.

11. The apparatus of claim 10, wherein the selected desired pressure modulation amplitude A includes a fixed amplitude.

12. The apparatus of claim 10, wherein the selected desired pressure modulation amplitude A includes a component equal to an elastance multiplied by an estimate of the subject's tidal volume.

13. The apparatus of claim 10, with further instructions for controlling the determination of a component of the selected desired pressure modulation amplitude A by:
    specifying an expected breath duration,
    specifying a preset pressure modulation amplitude to apply for said expected breath duration,
    calculating the actual breath duration of said subject, and
    calculating the component of said pressure modulation amplitude as a function of at least said specified preset pressure modulation amplitude multiplied by said calculated actual breath duration divided by the specified expected breath duration.

14. The apparatus of claim 10, with further instructions for controlling the calculation of phase in the respiratory cycle by:
    determining the extent to which the subject is adequately ventilated,
    to said extent setting the phase in the respiratory cycle in accordance with the subject's respiratory airflow, and to the converse extent setting the phase in accordance with a preset respiratory rate.

15. The apparatus of claim 10, wherein the instructions for controlling the calculation of phase in the respiratory cycle include controlling the sub-steps of:

estimating respiratory airflow, deriving a measure of mask leak stability, to the extent that mask leak is stable, calculating the phase in accordance with the estimate of respiratory airflow, and to the converse extent, calculating the phase in the respiratory cycle in accordance with a preset respiratory rate.

16. The apparatus of claim 10 wherein the selected desired pressure modulation amplitude includes a component chosen to servo-control the degree of ventilation to at least exceed a specified ventilation.

17. The apparatus of claim 16, in which said component is calculated with instructions controlling the sub-steps of:

calculating an error term proportional to the absolute value of estimated respiratory airflow minus twice said specified ventilation, and setting said component proportional to the time integral of said error term.

18. The apparatus of claim 17, wherein said time integral is clipped to fall between a preset minimum and a preset maximum.

* * * * *

UNITED STATES PATENT AND TRADEMARK OFFICE
CERTIFICATE OF CORRECTION

PATENT NO. : 6,484,719 B1
DATED : November 26, 2002
INVENTOR(S) : Michael Berthon-Jones It is certified that error appears in the above-identified patent and that said Letters Patent is hereby corrected as shown below:

<u>Title page,</u>
Item [73], Assignee, should read -- ResMed Ltd --.

Signed and Sealed this

Second Day of May, 2006

JON W. DUDAS
*Director of the United States Patent and Trademark Office*